(12) United States Patent
Budaragin et al.

(10) Patent No.: US 10,344,389 B2
(45) Date of Patent: Jul. 9, 2019

(54) LOW TEMPERATURE ELECTROLYTES FOR SOLID OXIDE CELLS HAVING HIGH IONIC CONDUCTIVITY

(71) Applicants: FCET, INC., Roswell, GA (US); UT-Battelle, LLC, Oak Ridge, TN (US)

(72) Inventors: Leonid V. Budaragin, Moscow (RU); Mark A. Deininger, Roswell, GA (US); Michael M. Pozvonkov, Cumming, GA (US); D. Morgan Spears, II, Atlanta, GA (US); Paul D. Fisher, Landis, NC (US); Arvid E. Pasto, Sparks, NV (US)

(73) Assignees: FCET, INC., Roswell, GA (US); UT-Battelle, LLC, Oak Ridge, TN (US)

( * ) Notice: Subject to any disclaimer, the term of this patent is extended or adjusted under 35 U.S.C. 154(b) by 79 days.

(21) Appl. No.: 15/597,126

(22) Filed: May 16, 2017

(65) Prior Publication Data
US 2018/0023205 A1    Jan. 25, 2018

Related U.S. Application Data

(63) Continuation of application No. 14/981,097, filed on Dec. 28, 2015, now abandoned, which is a
(Continued)

(51) Int. Cl.
*C25B 13/04*    (2006.01)
*H01M 8/0271*    (2016.01)
(Continued)

(52) U.S. Cl.
CPC ............... *C25B 13/04* (2013.01); *C25B 9/08* (2013.01); *C25B 9/10* (2013.01); *G01N 27/40* (2013.01);
(Continued)

(58) Field of Classification Search
CPC . C25B 13/04; C25B 9/08; C25B 9/10; H01M 8/1007; H01M 8/004;
(Continued)

(56) References Cited

U.S. PATENT DOCUMENTS 2,048,912 A    7/1936    Ziska et al.
2,141,477 A    12/1938    Loesch
(Continued)

FOREIGN PATENT DOCUMENTS

CA    2789281 C    11/2015
DE    295148 A5    10/1991
(Continued)

OTHER PUBLICATIONS

Simner et al. "Compressive mica seals for SOFC applications", Journal of Power Sources, vol. 102 (2001) pp. 310-316. (Year: 2001).*
(Continued)

*Primary Examiner* — Jonathan C Langman
(74) *Attorney, Agent, or Firm* — Thrive IP®; Jeremy M. Stipkala

(57) ABSTRACT

Methods for forming a metal oxide electrolyte improve ionic conductivity. Some of those methods involve applying a first metal compound to a substrate, converting that metal compound to a metal oxide, applying a different metal compound to the metal oxide, and converting the different metal compound to form a second metal oxide. Electrolytes so formed can be used in solid oxide fuel cells, electrolyzers, and sensors, among other applications.

9 Claims, 8 Drawing Sheets

Related U.S. Application Data continuation of application No. 13/578,195, filed as application No. PCT/US2011/024242 on Feb. 9, 2011, now abandoned.

(60) Provisional application No. 61/303,003, filed on Feb. 10, 2010.

(51) Int. Cl.
| | | |
|---|---|---|
| H01B 1/12 | (2006.01) | |
| H01M 8/1246 | (2016.01) | |
| H01M 8/1253 | (2016.01) | |
| H01M 8/126 | (2016.01) | |
| C25B 9/10 | (2006.01) | |
| H01M 8/243 | (2016.01) | |
| H01M 8/1007 | (2016.01) | |
| C25B 9/08 | (2006.01) | |
| G01N 27/40 | (2006.01) | |
| G01N 27/407 | (2006.01) | |
| H01M 8/00 | (2016.01) | |
| H01M 8/1006 | (2016.01) | |
| H01M 8/1016 | (2016.01) | |
| H01M 8/124 | (2016.01) | |

(52) U.S. Cl.
CPC ......... *G01N 27/4073* (2013.01); *H01B 1/122* (2013.01); *H01M 8/004* (2013.01); *H01M 8/0271* (2013.01); *H01M 8/1006* (2013.01); *H01M 8/1007* (2016.02); *H01M 8/1016* (2013.01); *H01M 8/126* (2013.01); *H01M 8/1246* (2013.01); *H01M 8/1253* (2013.01); *H01M 8/243* (2013.01); *H01M 2008/1293* (2013.01); *H01M 2300/0071* (2013.01); *H01M 2300/0074* (2013.01); *H01M 2300/0077* (2013.01); *H01M 2300/0091* (2013.01); *Y02E 60/525* (2013.01); *Y02P 70/56* (2015.11)

(58) Field of Classification Search
CPC ............. H01M 8/0271; H01M 8/1006; H01M 8/1016; H01M 8/1246; H01M 8/1253; H01M 8/126; H01M 8/243; H01M 2008/1293; H01M 2300/0071; H01M 2300/0074; H01M 2300/0077; H01M 2300/0091; G01N 27/40; G01N 27/4073; H01B 1/122; Y02P 70/56; Y02E 60/525
See application file for complete search history.

(56) References Cited

U.S. PATENT DOCUMENTS

| | | |
|---|---|---|
| 2,334,294 A | 11/1943 | Stevens |
| 2,470,796 A | 5/1949 | Stromquist |
| 2,530,110 A | 11/1950 | Woodyard |
| 2,792,807 A | 5/1957 | Cummings |
| 3,404,039 A | 10/1968 | Mitoff |
| 3,503,809 A | 3/1970 | Spacil |
| 3,673,452 A | 6/1972 | Brennen |
| 3,679,712 A | 7/1972 | Firestone |
| 3,773,555 A | 11/1973 | Cotton et al. |
| 3,947,292 A | 3/1976 | Jackovitz et al. |
| 3,962,490 A | 6/1976 | Ward |
| 3,967,149 A | 6/1976 | Eaton et al. |
| 3,984,717 A | 10/1976 | Romanowski et al. |
| 4,142,024 A | 2/1979 | Van Den Berghe et al. |
| 4,267,483 A | 5/1981 | Nakajima et al. |
| 4,279,974 A | 7/1981 | Nishio |
| 4,297,150 A | 10/1981 | Foster et al. |
| 4,307,061 A | 12/1981 | Sarholz |
| 4,318,894 A | 3/1982 | Hensel et al. |
| 4,358,892 A | 11/1982 | Turillon et al. |
| 4,530,340 A | 7/1985 | Totman |
| 4,686,201 A | 8/1987 | Porter et al. |
| 4,687,567 A | 8/1987 | Porter et al. |
| 4,743,793 A | 5/1988 | Toya et al. |
| 4,772,577 A | 9/1988 | Rittler |
| 4,786,267 A | 11/1988 | Toya et al. |
| 4,826,462 A | 5/1989 | Lenk |
| 4,828,934 A | 5/1989 | Pinkhasov |
| 4,853,582 A | 8/1989 | Sato et al. |
| 4,881,913 A | 11/1989 | Mann |
| 4,925,886 A | 5/1990 | Atkins et al. |
| 4,935,265 A | 6/1990 | Pike |
| 4,937,484 A | 6/1990 | Ishino |
| 4,961,917 A | 10/1990 | Byrne |
| 4,963,112 A | 10/1990 | Benedikt et al. |
| 4,963,390 A | 10/1990 | Lipeles et al. |
| 4,972,811 A | 11/1990 | Baresel et al. |
| 5,015,358 A | 5/1991 | Reed et al. |
| 5,021,398 A | 6/1991 | Sharma et al. |
| 5,028,467 A | 7/1991 | Maruyama et al. |
| 5,064,791 A | 11/1991 | Ohtsuka et al. |
| 5,073,410 A | 12/1991 | Paz-Pujalt |
| 5,100,632 A | 3/1992 | Dettling et al. |
| 5,106,706 A | 4/1992 | Singh et al. |
| 5,109,178 A | 4/1992 | Yoshida et al. |
| 5,130,210 A | 7/1992 | Iwasaki et al. |
| 5,274,298 A | 12/1993 | Cassidy et al. |
| 5,279,111 A | 1/1994 | Bell et al. |
| 5,312,585 A | 5/1994 | Jones |
| 5,342,703 A | 8/1994 | Kawasaki et al. |
| 5,413,642 A | 5/1995 | Alger |
| 5,423,285 A | 6/1995 | Paz de Araujo et al. |
| 5,468,679 A | 11/1995 | Paz de Araujo et al. |
| 5,472,795 A | 12/1995 | Aita |
| 5,494,700 A | 2/1996 | Anderson et al. |
| 5,518,603 A | 5/1996 | Furuhashi et al. |
| 5,551,994 A | 9/1996 | Schriever |
| 5,580,497 A | 12/1996 | Balachandran et al. |
| 5,601,869 A | 2/1997 | Scott et al. |
| 5,612,082 A | 3/1997 | Azuma et al. |
| 5,645,634 A | 7/1997 | Ogi et al. |
| 5,689,797 A | 11/1997 | Chelluri et al. |
| 5,699,035 A | 12/1997 | Ito et al. |
| 5,716,507 A | 2/1998 | Tanaka et al. |
| 5,753,385 A | 5/1998 | Jankowski et al. |
| 5,766,787 A | 6/1998 | Watanabe et al. |
| 5,805,973 A | 9/1998 | Coffinberry et al. |
| 5,817,436 A | 10/1998 | Nishijima et al. |
| 5,827,570 A | 10/1998 | Russell |
| 5,905,363 A | 5/1999 | Helbing et al. |
| 5,911,860 A * | 6/1999 | Chen .................. B01D 61/30 204/252 |
| 5,919,519 A | 7/1999 | Tallis |
| 5,952,769 A | 9/1999 | Budaragin |
| 5,968,463 A | 10/1999 | Shelef et al. |
| 5,976,458 A | 11/1999 | Sikka et al. |
| 5,990,416 A | 11/1999 | Windisch, Jr. et al. |
| 6,040,265 A | 3/2000 | Nunan |
| 6,051,529 A | 4/2000 | Brezny |
| 6,071,464 A | 6/2000 | Funaki et al. |
| 6,093,378 A | 7/2000 | Deeba et al. |
| 6,117,581 A | 9/2000 | Shelef |
| 6,127,202 A | 10/2000 | Kapur et al. |
| 6,139,921 A | 10/2000 | Taschner et al. |
| 6,153,160 A | 11/2000 | Voss et al. |
| 6,190,634 B1 | 2/2001 | Lieber et al. |
| 6,224,993 B1 | 5/2001 | Hartvigsen et al. |
| 6,268,014 B1 | 7/2001 | Eberspacher et al. |
| 6,294,261 B1 | 9/2001 | Sangeeta et al. |
| 6,320,375 B1 | 11/2001 | Cotton et al. |
| 6,328,779 B1 | 12/2001 | He et al. |
| 6,379,712 B1 | 4/2002 | Yan et al. |
| 6,416,818 B1 | 7/2002 | Aikens et al. |
| 6,426,315 B1 | 7/2002 | Bergstrom et al. |
| 6,448,190 B1 | 9/2002 | Hayashi et al. |
| 6,476,312 B1 | 11/2002 | Barnham |
| 6,500,733 B1 | 12/2002 | Stanbery |
| 6,559,372 B2 | 5/2003 | Stanbery |
| 6,593,213 B2 | 7/2003 | Stanbery |

(56) References Cited

U.S. PATENT DOCUMENTS

| | | | |
|---|---|---|---|
| 6,620,456 B2 | 9/2003 | Blanton et al. | |
| 6,624,213 B2 | 9/2003 | George et al. | |
| 6,663,983 B1 | 12/2003 | Darolia et al. | |
| 6,683,025 B2 | 1/2004 | Amendola et al. | |
| 6,686,489 B2 | 2/2004 | Celinska et al. | |
| 6,736,986 B2 | 5/2004 | Stanberry | |
| 6,769,152 B1 | 8/2004 | Crenshaw et al. | |
| 6,773,513 B2 | 8/2004 | Ludtka | |
| 6,824,883 B1 | 11/2004 | Benum et al. | |
| 6,899,966 B2 | 5/2005 | Benum et al. | |
| 6,921,557 B2 | 7/2005 | Jacobson et al. | |
| 6,969,484 B2 | 11/2005 | Horiguchi et al. | |
| 6,991,867 B1 | 1/2006 | Zhu | |
| 6,998,187 B2 | 2/2006 | Finnerty et al. | |
| 7,045,238 B2 | 5/2006 | Gottman et al. | |
| 7,083,710 B2 | 8/2006 | Scheer et al. | |
| 7,117,099 B2 | 10/2006 | Stassner et al. | |
| 7,156,979 B2 | 1/2007 | Benum et al. | |
| 7,161,124 B2 | 1/2007 | Kisner et al. | |
| 7,163,759 B2 | 1/2007 | Milliken et al. | |
| 7,211,292 B1 | 5/2007 | Budaragin | |
| 7,227,736 B2 | 6/2007 | Shioga et al. | |
| 7,229,597 B2 | 6/2007 | Patchett et al. | |
| 7,235,171 B2 | 6/2007 | Taniguchi | |
| 7,250,147 B2 | 7/2007 | Tour et al. | |
| 7,255,956 B2 | 8/2007 | McElroy et al. | |
| 7,271,333 B2 | 9/2007 | Fabick et al. | |
| 7,279,047 B2 | 10/2007 | Melnik et al. | |
| 7,300,684 B2 | 11/2007 | Boardman et al. | |
| 7,306,823 B2 | 12/2007 | Sagar et al. | |
| 7,318,763 B2 | 1/2008 | Tsakalakos et al. | |
| 7,351,488 B2 | 4/2008 | Visco et al. | |
| 7,488,392 B2 | 2/2009 | Benum et al. | |
| 7,491,376 B2 | 2/2009 | Barron et al. | |
| 7,645,543 B2 | 1/2010 | Visco et al. | |
| 7,718,221 B2 | 5/2010 | Budaragin et al. | |
| 8,623,301 B1 | 1/2014 | Deininger et al. | |
| 9,353,434 B2 | 5/2016 | Deininger et al. | |
| 9,670,586 B1 | 6/2017 | Deininger et al. | |
| 9,905,871 B2 | 2/2018 | Pozvonkov et al. | |
| 2001/0003010 A1 | 6/2001 | Pham et al. | |
| 2001/0041278 A1 | 11/2001 | Hashimoto et al. | |
| 2002/0004028 A1 | 1/2002 | Margrave et al. | |
| 2002/0006470 A1 | 1/2002 | Eberspacher et al. | |
| 2002/0041928 A1 | 4/2002 | Budaragin | |
| 2002/0160250 A1 | 10/2002 | Woods | |
| 2002/0182468 A1 | 12/2002 | Janousek et al. | |
| 2002/0187091 A1 | 12/2002 | Deevi | |
| 2003/0203267 A1* | 10/2003 | Chou | C04B 37/04 29/434 |
| 2004/0013924 A1 | 1/2004 | Park et al. | |
| 2004/0023101 A1 | 2/2004 | Jacobson et al. | |
| 2004/0033319 A1 | 2/2004 | Yamada et al. | |
| 2004/0048137 A1* | 3/2004 | Chou | C04B 37/04 429/511 |
| 2004/0061114 A1 | 4/2004 | Yan et al. | |
| 2004/0076867 A1 | 4/2004 | Day et al. | |
| 2004/0188323 A1 | 9/2004 | Tzatzov et al. | |
| 2004/0265664 A1* | 12/2004 | Badding | C04B 35/486 429/446 |
| 2005/0016848 A1 | 1/2005 | Sahimi et al. | |
| 2005/0089684 A1 | 4/2005 | Barron et al. | |
| 2005/0201919 A1 | 9/2005 | Yu et al. | |
| 2005/0247339 A1 | 11/2005 | Barnham et al. | |
| 2005/0257857 A1 | 11/2005 | Benum et al. | |
| 2005/0277024 A1 | 12/2005 | West et al. | |
| 2006/0008696 A1 | 1/2006 | Cha et al. | |
| 2006/0024547 A1 | 2/2006 | Waldbillig et al. | |
| 2006/0035130 A1 | 2/2006 | Noda et al. | |
| 2006/0040168 A1 | 2/2006 | Sridhar | |
| 2006/0063052 A1 | 3/2006 | Hu et al. | |
| 2006/0194117 A1 | 8/2006 | Paulsen | |
| 2006/0196419 A1 | 9/2006 | Tudhope et al. | |
| 2006/0198965 A1 | 9/2006 | Tudhope et al. | |
| 2006/0199057 A1* | 9/2006 | Hiwatashi | H01M 8/1253 429/489 |
| 2006/0231549 A1 | 10/2006 | Kisner et al. | |
| 2006/0234855 A1 | 10/2006 | Gorte et al. | |
| 2007/0015002 A1 | 1/2007 | Narula et al. | |
| 2007/0020502 A1 | 1/2007 | Cho et al. | |
| 2007/0059576 A1 | 3/2007 | Jacobson et al. | |
| 2007/0077440 A1 | 4/2007 | Gawalt | |
| 2007/0095662 A1 | 5/2007 | Suzuki | |
| 2007/0116966 A1 | 5/2007 | Mellot et al. | |
| 2007/0184322 A1 | 8/2007 | Huang et al. | |
| 2007/0227120 A1 | 10/2007 | Yodice et al. | |
| 2007/0237998 A1 | 10/2007 | Armstrong et al. | |
| 2007/0262059 A1 | 11/2007 | Boardman et al. | |
| 2007/0264542 A1 | 11/2007 | Devoe et al. | |
| 2007/0273070 A1 | 11/2007 | Badding et al. | |
| 2008/0029494 A1 | 2/2008 | Tudhope et al. | |
| 2008/0063587 A1 | 3/2008 | Strano et al. | |
| 2008/0118777 A1 | 5/2008 | Li et al. | |
| 2008/0131749 A1 | 6/2008 | Hilliard | |
| 2008/0299436 A1 | 12/2008 | Striker et al. | |
| 2008/0318092 A1 | 12/2008 | Sridhar et al. | |
| 2009/0087697 A1 | 4/2009 | Ramanathan et al. | |
| 2009/0098289 A1 | 4/2009 | Deininger et al. | |
| 2009/0218311 A1 | 9/2009 | Jiang et al. | |
| 2009/0226786 A1 | 9/2009 | Selcuk et al. | |
| 2010/0066036 A1 | 3/2010 | Cruse et al. | |
| 2010/0275979 A1 | 11/2010 | Maruyama | |
| 2012/0052405 A1 | 3/2012 | Crumm et al. | |
| 2012/0171596 A1 | 7/2012 | Hilliard | |
| 2013/0146469 A1 | 6/2013 | Budaragin et al. | |
| 2014/0017584 A1 | 1/2014 | Schade | |
| 2014/0319317 A1 | 10/2014 | Lai et al. | |
| 2016/0149249 A1 | 5/2016 | Pozvonkov et al. | |
| 2016/0168734 A1 | 6/2016 | Budaragin et al. | |
| 2017/0146481 A1 | 5/2017 | Pozvonkov et al. | |
| 2017/0162896 A1 | 6/2017 | Pozvonkov et al. | |
| 2018/0198148 A1 | 7/2018 | Pozvonkov et al. | |

FOREIGN PATENT DOCUMENTS

| | | |
|---|---|---|
| EP | 0414575 A1 | 2/1991 |
| EP | 0513982 A2 | 11/1992 |
| EP | 97/0682696 B1 | 12/1997 |
| EP | 01/1088908 A2 | 4/2001 |
| EP | 1 693 914 A1 | 8/2006 |
| EP | 1 103 080 B1 | 8/2008 |
| FR | 2617507 | 1/1989 |
| GB | 1049428 | 11/1966 |
| GB | 2460877 A | 12/2009 |
| JP | 2010-277771 A | 12/2010 |
| KR | 10-2010-0073833 A | 7/2010 |
| SU | 923232 A1 | 7/1980 |
| WO | 85/00997 | 3/1985 |
| WO | 92/010651 | 6/1992 |
| WO | 94/018299 | 8/1994 |
| WO | 97/025146 | 7/1997 |
| WO | 02/014657 A1 | 2/2002 |
| WO | 03/021004 | 3/2003 |
| WO | 03/070640 | 8/2003 |
| WO | 2004/104261 A1 | 12/2004 |
| WO | 2005/019324 | 3/2005 |
| WO | 2005/035951 A1 | 4/2005 |
| WO | 2007/009104 | 1/2007 |
| WO | 2008026803 A1 | 3/2008 |
| WO | 2008/123484 | 10/2008 |
| WO | 2008/130433 | 10/2008 |
| WO | 2009/126875 A2 | 10/2009 |
| WO | 2009/129380 A2 | 10/2009 |
| WO | 2011/100361 A2 | 8/2011 |
| WO | 2015009618 | 1/2015 |

OTHER PUBLICATIONS

English-language abstract for SU 923232 A1 Filippov et al.
Written Opinion for PCT/US2011/024242 dated Oct. 28, 2011.
Canadian Office Action in Canadian Patent Application No. 2,789,281, dated Nov. 15, 2013 (4 pages).

(56) References Cited

OTHER PUBLICATIONS

Canadian Office Action in Canadian Patent Application No. 2,789,281, dated Jul. 28, 2014 (3 pages).
Supplementary Partial European Search Report for European Application No. EP 11 74 2752, National Phase of PCT/US2011/024242, dated Mar. 3, 2015 (6 pages).
International Preliminary Report on Patentability for PCT/US2014/046519 dated Jan. 19, 2016 (9 pages).
Machine translation of Detailed Description of JP 5238610 B, related to JP 2010-277771 (12 pages).
Machine translation of Korean Patent Application Publication 10-2010-0073833 (8 pages).
Supplementary European Search Report for European Patent Application No. EP 11 74 2752 dated Jul. 3, 2015 (10 pages).
Notes, "ASM Fuel Cell Overview," (Oct. 2003) by Paul Fisher (2 pages).
Notes, "Fuel Cells 2004," (May 2004) by Paul Fisher (7 pages).
Notes, "CAMP/Nano-Network," (Jun. 2004) by Paul Fisher (2 pages).
Notes, "ASM/Columbus, OH," (Oct. 2004) by Paul Fisher (3 pages).
Notes, "Feb. 7, 2007," (Feb. 2007) by Paul Fisher (25 pages).
Notes, "Notes on Advances in SOFCs II," (Dec. 2007) by Paul Fisher (9 pages) (referencing "Advances in Solid Oxide Fuel Cells II," (N.P. Bansal et al., Eds., John Wiley & Sons 2007)).
Sandrine Colson-Inam, "Solid Oxide Fuel Cells Ready to Market?" FuelCellToday.com (Jan. 2004).
Sylvia Baron, "Intermediate Temperature (500-850) SOFC's Explained," FuelCellToday.com (Jan. 2004).
Gregor Knoner et al., "Enhanced oxygen diffusivity in interfaces of nanoctystalline ZrO2.Y2O3," PNAS vol. 100 No. 7, 3870-73 (Apr. 2003).
Matthew Seabaugh, Ph.D. et al., "Tailor Made," Ceramic Industry 24-27 (Apr. 2007).
"Development of a Portable Solid Oxide Fuel Cell," NanoDynamics, Inc. Presentation (May 2004).
William Smith, "Regenerative Fuel Cells for Renewable Energy Storage," Presentation (May 2004).
Zhenguo G. Yang et al., "Solid Oxide Fuel Cells, Materials for the Bipolar Plates of SOFC," Advanced Materials & Processes, 34-37 (Jun. 2003).
N. P. Brandon et al., "Development of Metal supported Solid Oxide Fuel Cells for Operation at 500-600 degrees celsius," Journal of Materials vol. 13, 253-56 (Jun. 2004).
Dillon D. Fong et al., "Ferroelectricity in Ultrathin Perovskite Films," Science vol. 304, 1650-53 (Jun. 2004).
"Revolution, Mobile, Powerful," Electrical Contractor 5-7 (Jun. 2004).
Zongping Shao et al., "A thermally self-sustained micro solid-oxide fuel-cell stack with high power density," Nature, 795-98 (Jun. 2005).
Emmeline Chen, "Solid-Oxide Fuel Cells Stack Up to Efficient Clean Power," Research Highlights, S&TR, 17-19 (Sep. 2002).
Material Solutions Conference Final Program, pp. 37, 65-67 (Oct. 2003).
Steven G. Chalk and S. R. Venkateswaran, "Is there a Continuing Role for the Federal Government in Fuel Cell R&D for Transportation?" 1998 Fuel Cell Seminar (Nov. 1998).
W.N. Lawless, "Honeycomb Fuel Cell," CeramPhysics. Inc. (Nov. 2003).
"World's Highest Efficiency for 1kW Class Power Generation," Kyocera (Dec. 2003) (accessed at http://global.kyocera.com/news/2003/1205.html on Aug. 2, 2006).
K. Muthukkumaran et al., "Ionic Conductivity Measurements in Gadolinia Doped Ceria," Int. Symp. Res. Students Mater. Sci. Eng. (Dec. 2004).
K. Huang, "Oxide-ion conducting ceramics for solid oxide fuel cells," Journal of Material Science, vol. 36, 1093-1098 (2001).
V. V. Kharton et al., "Ceria-Based Materials for Solid Fuel Cells," Journal of Materials Science, vol. 36, 1105-1117, (2001).
"Fuel Cells for Building and Vehicles," ORNL Review vol. 35 No. 2 (2002).
Austin Weber, "Fuel Cells Fact Not Fiction," Assembly 70-77 (2003).
"Cool fuel cells could revolutionize Earth's energy resources," Nanodynamics, Inc. (2004).
"Can gold be employed as a fuel cell catalyst," Catgold Issue No. 8, 3 (2005).
Michael Hill, "Material Trends in SOFC Systems," Ceramic Industry/Ceramic Energy 6-8 (2005).
Igor Kosacki, "Nanoscaled Oxide Thin Films for Energy Conversion," NATO Science Series II, 1-18 (2005).
E. Koep el al., "Microstructure & Electrochemical Properties" J. Power Sources 161, 250-255 (2006).
D. Todorovsky et al., "Spray-Pyrolysis, Deep and Spin-Coating Deposition of Thin Films and Their Characterization," Journal of the University of Chemical Technology and Metallurgy, vol. 41, No. 1, 93-96 (2006).
Binod Kumar et al., "Electrical Properties of Heterogeneously Doped Yttria Stabilized Zirconia" (undated).
C. Bentley et al., "Direct Fuel Cell Commercialization," Fuel Cell Energy, Inc. (undated).
Eric Wachsman, "Fundamentals of Ionic Transport," High Temperature Electrochemistry Center (accessed at http://hitech.mse.ufl.edu/Wachsman%201.htm on Jun. 23, 2006).
Henry Petroski, "Fuel Cells," American Scientist, vol. 91, 398-402 (2003).
Igor Kosacki et al., "Surface Interface-Related Conductivity in Nanometer Thick YSZ Films," Electrochemical and Solid-State Letters, 7, (12) A459-A461 (2004).
John Halloran et al., "Redefining Ceramic Fuel Cells," Ceramic Industry 25-28 (Apr. 2008).
E. Lara-Curzio "Mechanical Properties of tape cast nickel-based anode materials for solid oxide fuel cells before and after reduction in hydrogen," Acta. Mater. vol. 52 5747-5756 (2004).
"PAD: Polymer-Assisted Deposition of Metal-Oxide Films," Los Alamos National Laboratory (2006).
Maria Mercedes Gonzalez-Cuenca, Dissertation "Novel Anode Materials For Solid Oxide Fuel Cells" (2002).
Katsuyo Thornton et al.,"Nanotechnology for Fuel Cells and Batteries," NSF Workshop; Section 4 (accessed at www.cs.duke.edu . . . on Mar. 1, 2007.).
"Solid Oxide Fuel Cell Compositions," Praxair (accessed at www.praxair.com on Sep. 14, 2006).
"New Metal-Oxide Process," Semiconductor International (2005) (accessed at www.reed-electronics.com on Jun. 29, 2007).
S. Kang et al., "Thin-Film Solid Oxide Fuel Cells on Porous Nickel Substrates with Multistage Nanohole Array," Journal of The Electrochemical Society, 153 (3) A554-A559 (2006).
Sol Gel Technology, (accessed at www.chemat.com/html/solgel.html on Nov. 7, 2003).
Tatsumi Ishihara et al., "Electrolytes," in High Temperature Solid Oxide Fuel Cells, Fundamentals, Design and Applications, Chapter 4, Elsevier (2003).
"Solid Oxide Fuel Cell," Wikipedia.org (accessed Oct. 3, 2007).
J. Britt, Photovoltaic Manufacturing Cost and Throughput Improvements for Thin Film CIGS-Based Molecules: Final Technical Report, Apr. 2002, National Renewable Energy Laboratories.
G.S. Chai et al., "Synthesis of Ordered, Uniform, Macroporous Carbons with Mesoporous Walls Templated by Aggregates of Polystyrene Spheres and Silica Particles for Use as Catalyst Supports in Direct Methanol Fuel Cells," Adv. Mater. 2004, 16, No. 22, 2057-2061.
R. Goettler, "Overview of the Rolls-Royce SOFC Technology and SECA Program," Jul. 14, 2009.
G.C. Hood et al., "Aluminum Acetates and Propionates—Their Preparation and Composition," 72 J. Am. Chem. Soc., 2094-95 (1950).
Narayanan et al., "Synthesis of Soluble Aluminium Carboxylates Directly from Aluminium Hydroxide," J. Mater. Chem., 10 (2000) 2097-104.
M. Brown, "Taking the Heat," Frontiers (Apr. 2004) pp. 34-37.

(56) References Cited

OTHER PUBLICATIONS

G. Can De Goor et al., "Chromophore-Zeotype Composites: Direct Synthesis of an Array of Strictly Aligned Metal-Organic Complex Chromophores in a Crystalline Silica Matrix," Adv. Mater. 1996, 8, No. 1, 65-69.
Hernadi et al., "Synthesis of MWNT-based Composite Materials with Inorganic Coating," 51 Acta Materialia (2003) pp. 1447-1452.
Garcia-Barriocanal et al., Colossal Ionic Conductivity at Interfaces of Epitaxial ZrO2:Y2O3/SrTiO3 Heterostructures, 321 Science 676 (2008), with Supporting Online Material.
Chen et al., "Photocatalytic Degradation of Methylene Blue by CNT/TiO2 Composites Prepared from MWCNT and Titanium n-Butoxide with Benzene," 45 J. Korean Ceram. Soc. (2008) 651-57.
Zhu et al., "Preparation and Characterization of New Photocatalyst Combined MWCNTs with TiO2 Nanotubes," 17 Trans. Nonferrous Met. Soc. China (2007) s1117-s1121.
Latu-Romain et al., "Growth Parameters and Shape Specific Synthesis of Silicon Nanowires by the VLS Method," 10 J. Nanopart Res. (2008) 1287-91.
Civale et al., "Aspects of Silicon Nanowire Synthesis by Aluminum-Catalyzed Vapor-Liquid-Solid Mechanism," Proceedings of 7th Annual Workshop on Semiconductor Advances for Future Electronics (SAFE 2004), Nov. 25-26, 2004, Veldhoven, The Netherlands,Publ. STW, ISBN 90-73461-43-X, pp. 692-696.
Kanai et al., "Semiconductor Testing Probe Utilizing Silicon Whisker Grown by VLS (Vapor Liquid Solid) Method," Tokyo Cathode Laboratory (Jun. 6, 2001) (available at: http://www.swtest.org/swtw_library/2001proc/PDF/S7_01.pdf (accessed Feb. 20, 2009).
Hu et al., "TiO2 Thin Films Prepared from Aqueous Solution and Their Sterilizing Capability," 7 J. Ceram. Proc. Res., (2006) 49-52.
Kilner, J.A., "Feel the Strain," Nature Materials, vol. 7 (2008) 838-839.
"Zirconia Toughened Alumina ZTA—Properties and Applications of ZTA by Dynamic Ceramic Ltd." (available at http://www.azom.com/details.asp?ArticleID=3303)(accessed Dec. 7, 2007).
"High Emissivity Coating Technology Improves Heater Performance" (available at http://www.cisoilgas.com)(2012) (accessed May 30, 2012).
Report description and table of contents, "Curtailing Coke Formation in Ethylene Furnace Tubes" Nexant, Inc., Jun. 4, 2003 (available at http://nexant.ecnext.com/coms2/gi_0255-146/Curtailing-Coke-Formation-in-Ethylene.html (accessed Sep. 27, 2007).
Zervos et al., "Printed and Thin Film Photovoltaics and Batteries," (IDTechEx, Jun. 2008) (available at http://www.idtechex.com/research/reports/printed_and_thin_film_photovoltaics_and_batteries_000172.asp) (accessed Mar. 5, 2009).
Z.L. Wang, T.S. Ahmad and M.A. El-Sayed, "Steps, ledges and kinks on the surfaces of platinum nanoparticles of different shapes," Surface Science, 380,302 (1997).
G. Rupprechter, K. Hayek and H. Hofmeister, "Electron microscopy of thin-film model catalysts: activation of alumina-supported rhodium nanoparticles," Journal of Catalysts, 173, 409 (1998).
Zhong Lin Wang and Xiangdong Feng, "Polyhedral shapes of CeO2 nanoparticles," J. Phys. Chem. B, 107, 13563-66 (2003).
Roberet Schlogl and Shaifah Bee ABD Hamid, "Nanocatalysts: Mature Science Revisited or Something Really New?," Angew. Chem. Int. Ed., 43, 1628 (2004).
M. Adlim, Mohamad Abu Bakar, Kong Yong Liew and Jamil Ismail, "Synthesis of chitosan-stabilized platinum and palladium nanoparticles and their hydrogenation activity," Journal of Molecular Catalysis A, 212, 141 (2004).
V.K. Kapur, A. Bansal, O. I. Asensio, P. Le and N. K. Shigeoka, "Fabrication of CIGS Solar Cells via Printing of Nanoparticle Precursor Inks," International Solar Electric Technology Inc. (ISET) (2004).
Tsai et al., "Low-Temperature Solid-Oxide Fuel Cells Utilizing Thin Bilayer Electrolytes," J. Electrochem. Soc., vol. 144, No. 5 (1997) pp. L130-L132.
Ghosh et al., "Glass-Ceramic Sealants for Planar IT-SOFC: a Bilayered Approach for Joining Electrolyte and Metallic Interconnect," J. Electrochem. Soc., vol. 155, No. 5 (2008) B473-B478.
K. An, "Mechanical Properties and Electrochemical Durability of Solid Oxide Fuel Cells," Ph.D. Dissertation, Virginia Polytechnic Institute and State University (2003).
A. Krishnan, "Solid Oxide Membrane Process for the Direct Reduction of Magnesium from Magnesium Oxide," Ph.D. Dissertation, Boston University (2006).
Fujishima et al., 70 Pure Appl. Chem. (1998) 2177-87.
S. Hofmann, "Gold catalyzed growth of silicon nanowires by plasma enhanced chemical vapor deposition," Journal of Applied Physics vol. 94, No. 9 (2003).
Rosnita Muhammad, Zulkafli Othaman, Samsudi Sakrani Yussof Wahab, "Vapor-liquid solid mechanism using gold colloids for the growth of GaAs nanowires," Physics Department, Faculty of Science, Universiti Teknologi Malaysia, 81310 UTM, Skudai, Johor (2008).
Igor Kosacki, Toshio Suzuki, Harlan U. Anderson, Philippe Colomban, "Raman scattering and lattice defects in nanocrystalline CeO2 thin films," Solid State Ionics 149 (2002) 99-105.
Xu, Zhigang et al., "Preparation and properties of YSZ electrolyte thin films via liquid fuel combustion chemical vapor deposition," NSF Center for Advanced Materials and Smart Structures, North Carolina A and T State, Ceramic Engineering and Science Proceedings, (2002), 23(3), 711-718.
Hampikian, J.M. et al., "The combustion chemical vapor deposition of high temperature materials," Materials Science and Engineering A267 (1999) pp. 7-18.
Kettering University, "Fuel Cell Background Information," 2011(?) (available at: http://orgs.kettering.edu/altfuel/fcback.htm)(Accessed May 6, 2016)(11 pages).
Evans et al., "Review on micro-fabricated micro-solid oxide fuel cell membranes," Journal of Power Sources, 194, (2009) 119-129.
J. Fleig et al., "Electrodes and electrolytes in micro-SOFCs: a discussion of geometrical constrains," Solid State Ionics, 174 (2004) pp. 261-270.
Unpublished U.S. Appl. No. 15/151,592, filed May 11, 2016 (62 pages).
Office Action in U.S. Appl. No. 14/093,445 dated Jan. 13, 2016 (16 pages).
Final Office Action in U.S. Appl. No. 14/093,445 dated Jun. 9, 2016 (26 pages).
Office Action in U.S. Appl. No. 12/420,457 dated Mar. 1, 2012 (5 pages).
Final Office Action in U.S. Appl. No. 12/420,457 dated May 22, 2013 (11 pages).
Office Action in U.S. Appl. No. 12/420,457 dated Sep. 24, 2013 (9 pages).
Final Office Action in U.S. Appl. No. 10/440,802 (Now U.S. Pat. No. 7,718,221) dated Oct. 23, 2008 (12 pages).
Office Action in U.S. Appl. No. 13/578,195 dated Nov. 7, 2013 (12 pages).
Final Office Action in U.S. Appl. No. 13/578,195 dated Jul. 9, 2014 (11 pages).
Unpublished U.S. Appl. No. 14/104,994, filed Dec. 12, 2013 (114 pages).
Office Action in U.S. Appl. No. 14/104,994 dated May 13, 2016 (16 pages).
Unpublished U.S. Appl. No. 15/149,866, filed May 9, 2016 (114 pages).
Final Office Action in U.S. Appl. No. 14/104,994 dated Sep. 8, 2016 (20 pages).
Office Action in U.S. Appl. No. 14/981,097 dated Nov. 21, 2016 (8 pages).
Communication from European Patent Office in EP Patent Application No. 11 742 752.6 dated Nov. 8, 2016 (4 pages).
Extended European Search Report from European Patent Office in EP Patent Application No. 14 826 675.2 dated Nov. 17, 2016 (9 pages).
Office Action in U.S. Appl. No. 14/904,570 dated Mar. 15, 2017 (5 pages).

(56) References Cited

OTHER PUBLICATIONS

Office Action in U.S. Appl. No. 14/104,994 dated Apr. 17, 2017 (17 pages).
Communication from European Patent Office in EP Patent Application No. 11 742 752.6 dated Jun. 7, 2017 (5 pages).
Office Action in U.S. Appl. No. 15/149,866 dated Dec. 29, 2016 (9 pages).
Final Office Action in U.S. Appl. No. 15/149,866 dated Jul. 18, 2017 (9 pages).
Office Action in U.S. Appl. No. 15/396,730 dated Aug. 9, 2018 (13 pages).
Office Action in Canadian Pat. App. No. 2,899,575 dated Jul. 11, 2017 (4 pages).
Final Office Action in U.S. Appl. No. 14/104,994 dated Nov. 1, 2017 (16 pages).
Ballee, E., et al., "Synthesis of a Thi-Layered Ionic Conductor, $CeO_2$-$Y_2O_3$, by Atomic Layer Deposition in View of Solid Oxide Fuel Cell Applications," Chem. Mater. 21, (2009) 4614-4619.
Office Action in U.S. Appl. No. 15/433,379 dated Sep. 20, 2018 (17 pages).
Office Action in European Pat. App. No. 14 826 675.2 dated Oct. 16, 2017 (6 pages).
Office Action in U.S. Appl. No. 14/904,570 dated Nov. 13, 2017 (6 pages).
Final Office Action in U.S. Appl. No. 14/904,570 dated Sep. 15, 2017 (8 pages).
Office Action in Canadian Pat. App. No. 2,899,575 dated Apr. 5, 2019 (3 pages).
Final Office Action in U.S. Appl. No. 15/433,379 dated Apr. 16, 2019 (16 pages).
Jeffrey J. Urban et al., "Synthesis of Single-Crystalline Perovskite Nanorods Composed of Barium Titanate and Strontium Titanate," J. Am. Chem. Soc., 124(7) (2002) 1186-1187.

\* cited by examiner

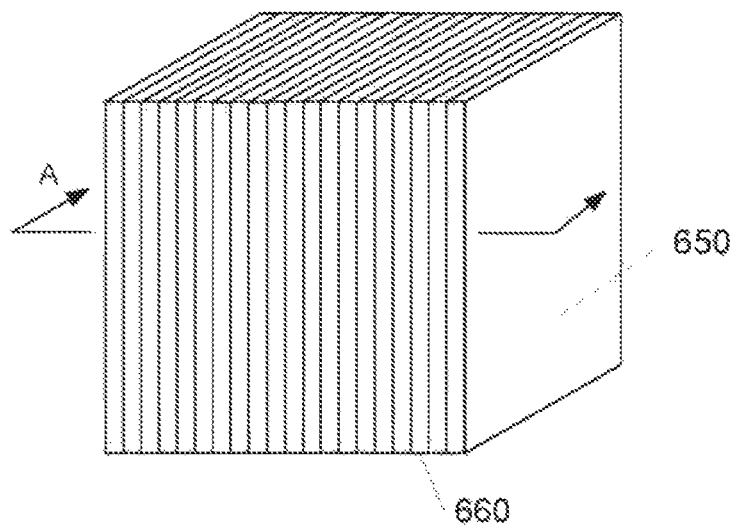
Fig. 6A
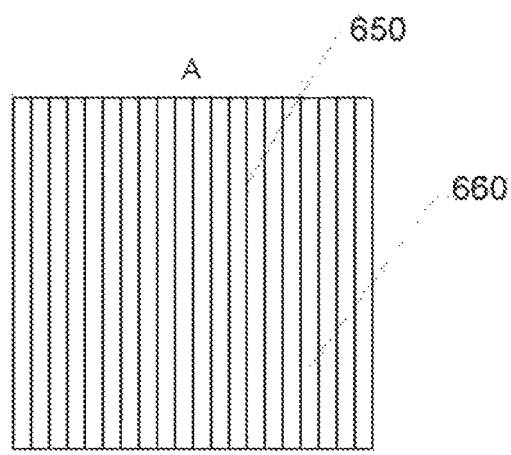
Fig. 6B
Figure 6

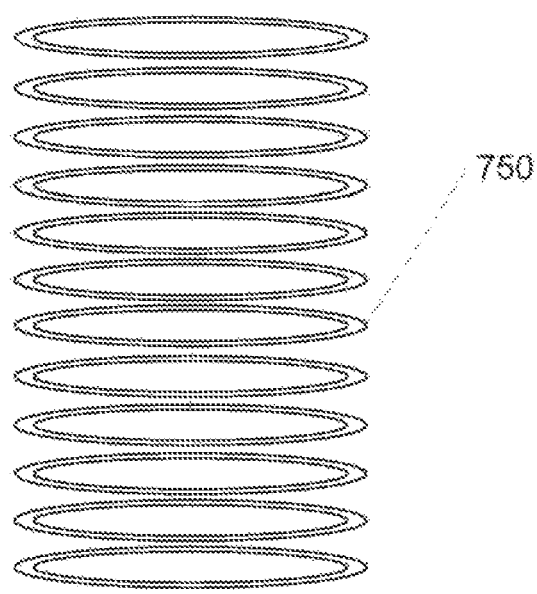
Fig. 7A
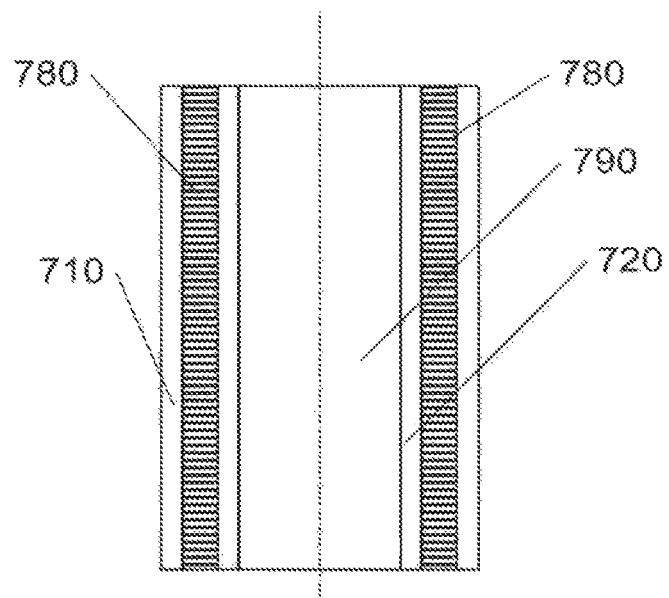
Fig. 7B
Figure 7.

LOW TEMPERATURE ELECTROLYTES FOR SOLID OXIDE CELLS HAVING HIGH IONIC CONDUCTIVITY

CROSS REFERENCE TO RELATED APPLICATIONS

The present application claims benefit of priority of and is a continuation of U.S. Non-Provisional patent application Ser. No. 14/981,097, filed on Dec. 28, 2015, and entitled, "LOW TEMPERATURE ELECTROLYTES FOR SOLID OXIDE CELLS HAVING HIGH IONIC CONDUCTIVITY," which claims benefit of priority of, and is a continuation of U.S. Non-Provisional patent application Ser. No. 13/578,195, filed on Aug. 9, 2012 and having a § 371 date of Jan. 28, 2013, which represents the National Stage under 35 U.S.C. § 371 of International Patent Application No. PCT/US2011/024242, filed internationally on Feb. 9, 2011 and entitled, "LOW TEMPERATURE ELECTROLYTES FOR SOLID OXIDE CELLS HAVING HIGH IONIC CONDUCTIVITY," which in turn claims benefit of priority under PCT Article 8 and 35 U.S.C. § 119(e) of U.S. Provisional Application No. 61/303,003, filed on Feb. 10, 2010, entitled, "LOW TEMPERATURE ELECTROLYTES FOR SOLID OXIDE CELLS HAVING HIGH IONIC CONDUCTIVITY." The foregoing Ser. Nos. 14/981,097, 13/578,195, PCT/US2011/024242, and 61/303,003 applications are incorporated herein by reference in their entireties.

STATEMENT REGARDING FEDERALLY-SPONSORED RESEARCH AND DEVELOPMENT

This invention was made with government support awarded by the Department of Energy and administered by Oak Ridge National Laboratory/UT Battelle. The government has certain rights in the invention.

FIELD OF THE INVENTION

The present invention relates to electrical energy systems such as fuel cells, electrolyzer cells, and sensors, and, in particular, to solid oxide fuel cells, solid oxide electrolyzer cells, solid oxide sensory and components of any of the foregoing.

BACKGROUND OF THE INVENTION

Solid oxide fuel cells, otherwise known as ceramic fuel cells, present an environmentally friendly alternative to mainstream electrical energy production processes involving the combustion of fossil fuels. Solid oxide fuel cells enable the catalytic conversion of chemical energy stored in hydrogen into electrical energy without the concomitant release of greenhouse gases. The generation of electrical current by a solid oxide fuel cell using a hydrogen fuel results in the production of water as opposed to the production carbon dioxide, nitrous oxides, and/or sulfur dioxides associated with the combustion of fossil fuels.

In addition to hydrogen solid oxide fuel cells are operable to function on a wide variety of fuel sources. Fuel sources in addition to hydrogen include hydrocarbons such as methane, natural gas, and diesel fuel. Hydrocarbon fuel sources are reformed into hydrogen for use with solid oxide fuel cells. Hydrocarbon reforming can be administered prior to entry into the fuel electrode or can be administered at the fuel electrode of a solid oxide fuel cell. The ability to function on a wide variety of fuels distinguishes solid oxide fuel cells from other fuel cells which lack the ability to operate on various fuels. Furthermore, the ability of solid oxide fuel cells to administer hydrocarbon feedstock reformation frees such fuel cells from the limitations associated with hydrogen production and distribution.

Currently, solid oxide fuel cells operate at high temperatures ranging from about 800° C. to 1000° C. As a result of high operating temperatures, solid oxide fuel cells require the use of exotic materials which can withstand such operating temperatures. The need for exotic materials greatly increases the costs of solid oxide fuel cells, making their use in certain applications cost-prohibitive. High operating temperatures exacerbate stresses caused by differences in coefficients of thermal expansion between components of a solid oxide fuel cell if the operating temperature could be lowered, numerous advantages could be realized. First, less expensive materials and production methods could be employed. Second, the lower operating temperature would allow greater use of the technology. Third, energy needed to heat and operate the fuel cell would be lower, increasing the overall energy efficiency. Significantly, the high operating temperature is required because of poor low temperature ion conductivity.

Proton exchange membrane ("PEM") fuel cells enjoy operational temperatures in the range 50-220° C. Typically relying on special polymer membranes to provide the electrolyte. PEM cells transmit protons across the electrolyte, rather than oxygen ions as in solid oxide fuel cells. However, high proton conductivity requires precise control of hydration in the electrolyte. If (the electrolyte becomes too dry, proton conductivity and cell voltage drop. If the electrolyte becomes too wet, the cell becomes flooded. Electro-osmotic drag complicates hydration control protons migrating across the electrolyte "drag" water molecules along, potentially causing dramatic differences in hydration across the electrolyte that inhibit cell operation. Accordingly, it would be advantageous to obtain the low operating temperatures of the PEM fuel cell without the need to maintain strict control over electrolyte hydration.

In certain circumstances, a solid oxide fuel cell can operate "in reverse" to electrolyze water into hydrogen gas and oxygen gas by inputting electrical energy in other circumstances, a solid oxide electrolyzer cell can be designed primarily for use as a hydrolyzer, generating hydrogen and oxygen for later use. In still other circumstances, an electrolyzer cell can be used for other purposes, such as extraction of metal from ore and electroplating. In conventional electrolyzers, electrical energy is lost in the electrolysis reaction driving the diffusion of ions through the electrolyte and across the distance between the electrodes. Also, the ability to conduct electrolysis at higher temperatures would improve the efficiency of the electrolysis. However, at higher temperatures, electrolyzers face similar thermal stresses and cracking caused by differences in coefficients of thermal expansion between components of the solid oxide electrolyzer cell. Accordingly, better matching of coefficients of thermal expansion and lower operating temperatures are desired for electrolyzer cells.

A lambda sensor is a device typically placed in the exhaust stream of an internal combustion engine to measure the concentration of oxygen. That measurement allows regulation of the richness or leanness of the fuel/air mixture flowing into the engine. If the fuel/air stream contains too much oxygen, the quantity $\lambda$ is greater than 1, and the mixture is too lean. If the fuel/air stream contains too little oxygen, then $\lambda<1$ and the mixture is too rich. $\lambda$ equals 1, the ideal situation, when the mixture contains a stoichiometrically equivalent concentration of oxygen and hydrocarbon to allow for complete combustion. A lambda sensor positioned in the exhaust stream detects the amount of oxygen in the combustion products, thereby providing feedback regarding richness or leanness. Lambda sensors and other sensors rely on the diffusion of oxygen anions ($O^{2-}$) and other ions through barrier materials in ways similar to the manner in which oxygen anions diffuse through a solid electrolyte of a solid oxide fuel cell. Moreover, given the high operating temperature of lambda sensors and similar devices, sensors face thermal stresses, cracking, and determination issues similar to those facing fuel cells and electrolyzers. Accordingly embodiments of the present invention provide for improved sensor technology by addressing ionic conductivity and mismatching of coefficients of thermal expansion, among other reasons.

It has recently been reported that adjacent atomically flat layers of strontium titanate (STO) with yttria-stabilized zirconia (YSZ) produce an interface that has a dramatically higher ionic conductivity for oxygen anions. J. Garcia-Barriocanal et al., "Colossal Ionic Conductivity at Interfaces of Epitaxial $ZrO_2:Y_2O_3/SrTiO_3$ Heterostructures," 321 SCIENCE 676 (2008). Those authors concluded that growing thin epitaxial layers of YSZ on epitaxial STO caused the YSZ to conform under strain to the crystal structure of the STO, thereby creating voids in the YSZ crystal structure at the interface between the two materials. Those voids allowed an increase of oxygen ionic conductivity of approximately eight orders of magnitude relative to bulk YSZ at 500 K (227° C.).

In view of the foregoing problems and disadvantages associated with the high operating temperatures of solid oxide cells, it would be desirable to provide solid oxide cells that can demonstrate lower operating temperatures. In addition, providing solid oxide cells and components that better tolerate higher temperatures would be advantageous. Moreover, the efficiency losses due to the thickness of electrolytes make thinner electrolytes desirable. Furthermore, it is also desirable to construct metal oxide electrolytes having dramatically higher ionic conductivities. Large-scale production of metal oxide electrolytes would be facilitated if higher ionic conductivities could be achieved without requiring epitaxial growth of electrolyte materials.

SUMMARY

Applicants have unexpectedly discovered methods for fabricating metal oxide electrolytes for use in solid oxide cells that do not require painstaking epitaxial growth of electrolyte materials, in some embodiments of the present invention in other embodiments, unexpectedly high ionic conductivities can be observed in still other embodiments, unexpectedly high ionic conductivities can be observed at relatively low temperatures. Without wishing to be bound by theory, certain embodiments exhibit enhanced ionic conduction by providing domain boundaries (for example, crystal grain boundaries) disposed in a direction parallel to the desired ionic conduction.

As used herein, "solid oxide cell" means any electrochemical cell that contains a metal oxide electrolyte, and refers to, for example, solid oxide fuel cells, solid oxide electrolyzer cells, cells that can operate as a fuel cell and an electrolyzer cell, and solid oxide sensors.

"Metal oxide electrolyte" indicates a material, useful as an electrolyte in a solid oxide cell, that contains a metal oxide. The metal oxide electrolyte can contain one or more metal oxides dispersed in any suitable manner. For example, two metal oxides can be mixed together in the manner of $ZrO_2:Y_2O_2$, or $SrTiO_3$. For another example, two metal oxides can be present in discrete domains having an abrupt interface between them. In yet another example, two metal oxides can form a diffuse interface between them. Still further examples provide more than two metal oxides present in a metal oxide electrolyte, such as, for example, $ZrO_2:Y_2O_2/SrTiO_3$. The metal oxide electrolyte optionally further contains a material other than a metal oxide. Examples include, but are not limited to, metals, semiconductors, insulators (other than metal oxides), carbides, nitrides, phosphides, sulphides, and polymers, and combinations thereof in the context of this disclosure, silicone polymers are polymers, while silica is a metal oxide. When used in this document, the meaning of "material" includes metal oxides unless otherwise indicated.

Accordingly, some embodiments of the present invention relate to methods of enhancing ionic conductivity in a metal oxide electrolyte comprising a first material and a metal oxide comprising:
applying a metal compound to the first material; and
converting at least some of the metal compound to form the metal oxide;
wherein the first material and the metal oxide have an ionic conductivity greater than the bulk ionic conductivity of the first material and of the metal oxide.

Other embodiments provide a metal oxide electrolyte composing:
a first material and a metal oxide, wherein the metal oxide is formed by applying a metal compound to the first material; and
converting at least some of the metal compound to form the metal oxide,
wherein the first material and the metal oxide have an ionic conductivity greater than the bulk ionic conductivity of the first material and of the metal oxide.

Still other embodiments provide methods for forming a metal oxide electrolyte, comprising:
applying a metal compound to a first material in powder form; and
converting at least some of the metal compound to form a metal oxide, thereby forming the metal oxide electrolyte;
wherein the metal oxide electrolyte has an ionic conductivity greater than the bulk ionic conductivity of the first material and of the metal oxide.

Additional embodiments provide methods for forming a metal oxide electrolyte, comprising:
applying a first metal compound to a substrate;
converting at least some of the first metal compound to form a first metal oxide on the substrate;
applying a second metal compound to the substrate comprising the first metal oxide; and
converting at least some of the second metal compound to form a second metal oxide on the substrate comprising the first metal oxide,
thereby forming the metal oxide electrolyte;
wherein the metal oxide electrolyte has an ionic conductivity greater than the bulk ionic conductivity of the first metal oxide and of the second metal oxide.

Still other embodiments provide methods for forming a metal oxide electrolyte, comprising:
applying a metal compound to a first material in nanobar form; and
converting at least some of the metal compound to form a metal oxide, thereby forming the metal oxide electrolyte;

wherein the metal oxide electrolyte has an ionic conductivity greater than the bulk ionic conductivity of the first material and of the metal oxide. Nanobars, in the present invention, comprise single walled nanotubes, multiwalled nanotubes, nanorods and combinations thereof. In certain embodiments, the nanobars comprise a material susceptible to orient in an electric or magnetic field, such as, for example ferroelectric materials, ferromagnetic materials, and paramagnetic materials, alone or in combination. In one embodiment, a nanobar has a perovskite crystal structure. In another embodiment, the nanobar further composes a derivative that imparts a dipole moment to the nanobar. In yet another embodiment, a nanobar comprises a segnetoelectric material, such as, for example, those disclosed in International Application Publication No. WO/2005/019324, which is incorporated herein by reference in its entirety. A segnetoelectric material exhibits a polarization even in the absence of an external electric field. Such spontaneous polarization is caused by the crystal structure of the material, and a given material may have segnetoelectric and nonsegnetoelectric crystal phases. Barium titanate, for example, exhibits segnetoelectric behavior. Piezoelectric materials may also exhibit segnetoelectric behavior. In further embodiments, one or more orienting forces can be applied, such as, for example, brushing, spin coating, a magnetic field, an electric field, or a combination thereof, to cause the nanobars to assume an orientation in the electrolyte. The orienting force can be applied before and/or during the converting.

Certain other embodiments of the present invention provide methods for forming a metal oxide electrolyte comprising:
applying a metal compound to a thin sheet; and
converting at least some of the metal compound to form a metal oxide on the thin sheet, thereby forming the metal oxide electrolyte;
wherein the metal oxide electrolyte has an some conductivity greater than the bulk ionic conductivity of the thin sheet and of the metal oxide. In some embodiments, a thin sheet comprises mica.

Yet further embodiments provide a solid oxide cell, comprising:
an inner tubular electrode having an outer surface;
an outer electrode; and
a metal oxide electrolyte adapted to provide ionic conductivity between the inner tubular electrode and the outer electrode;
wherein the metal oxide electrolyte composes a plurality of thin sheets oriented substantially perpendicular to the outer surface of the inner tubular electrode, and a metal oxide contacting the thin sheets.

Certain embodiments of the present invention provide enhanced ionic conductivity through the metal oxide electrolyte, thereby allowing a lower operating temperature. By lowering the operating temperature of a solid oxide cell, loss exotic and easier-to-fabricate materials can be utilized in the construction of the cell leading to lower production costs. Thus, some embodiments of the present invention provide solid oxide cells and components thereof employing simpler, less-expensive materials than the current state of the art. For example, it the operating temperature of a solid oxide cell can be lowered, then metals can be used for many different components such as electrodes and interconnects. At these lower operating temperatures, metals have more desirable mechanical properties, such as higher strength, than ceramics. In addition, this higher strength can allow metal components also to have a higher degree of porosity. Current ceramic electrode materials allow for porosity levels in the range of 30% to 40%, incorporating higher porosity levels in ceramic materials renders them too structurally weak to support cell construction. However, through the use of certain metals or metal carbides, the porosity of an electrode can be provided in the higher range of 40% to 80% and yet retain sufficient mechanical strength for cell construction. Some embodiments of the present invention provide an electrode having a porosity ranging from about 40% to about 80%.

Lower production costs in addition to lower operating temperatures provide the opportunity for solid oxide cells to find application in a wider variety of fields. Additionally, lower operating temperatures reduce degradative processes such as those associated with variances in coefficients of thermal expansion between dissimilar components of the cell. Accordingly, some embodiments provide means and methods for reducing a degradation process in a solid oxide cell.

Still other embodiment produce a desirable surface catalytic effect. For example, by using the process of some embodiments of the present invention, thin films of metal oxides and pure metals (or other metal compounds) can be formed on the exposed pore surfaces of electrodes to produce more chemically active sites at triple phase boundaries where either fuel-gas (as in the case of the anode electrode) or gaseous oxygen (as in the case of the cathode electrode) come into contact with the solid (yet porous) electrodes in a fuel cell.

Other embodiments provide methods of making solid oxide cells and components thereof. Certain embodiments provide methods of making solid oxide cells and components thereof applying temperatures dramatically below those of current methods. Current methods of making solid oxide fuel cells involve the sintering of ceramic and/or metal powders. High sintering temperatures during fabrication of various components, such as the electrolyte, can compound problems associated with variances in coefficients of thermal expansion.

These and other embodiments are described in greater detail in the description which follows.

BRIEF DESCRIPTION OF THE DRAWINGS

The figures are not necessarily to scale, and should not be construed as limiting. Some details may be exaggerated to aid comprehension.

FIG. 6 comprises FIG. 6A and FIG. 6B. FIG. 6A partially depicts another embodiment of the present invention, a plurality of thin sheets 650 comprising metal oxide 660 between the thin sheets 650. FIG. 6B depicts a view of cut "A" from FIG. 6A.

FIG. 7 comprises FIG. 7A and FIG. 7B. FIG. 7A partially depicts another embodiment of the present invention, a plurality of thin sheets 750 in annular form arranged substantially concentrically and substantially parallel. FIG. 7B partially depicts a side cut-away view of a tubular solid oxide cell according to another embodiment of the present invention. A plurality of thin sheets such as those depicted in FIG. 7A form a metal oxide electrolyte 780 between two tubular concentrically-arranged electrodes 710, 720.

DETAILED DESCRIPTION

Figure 1:
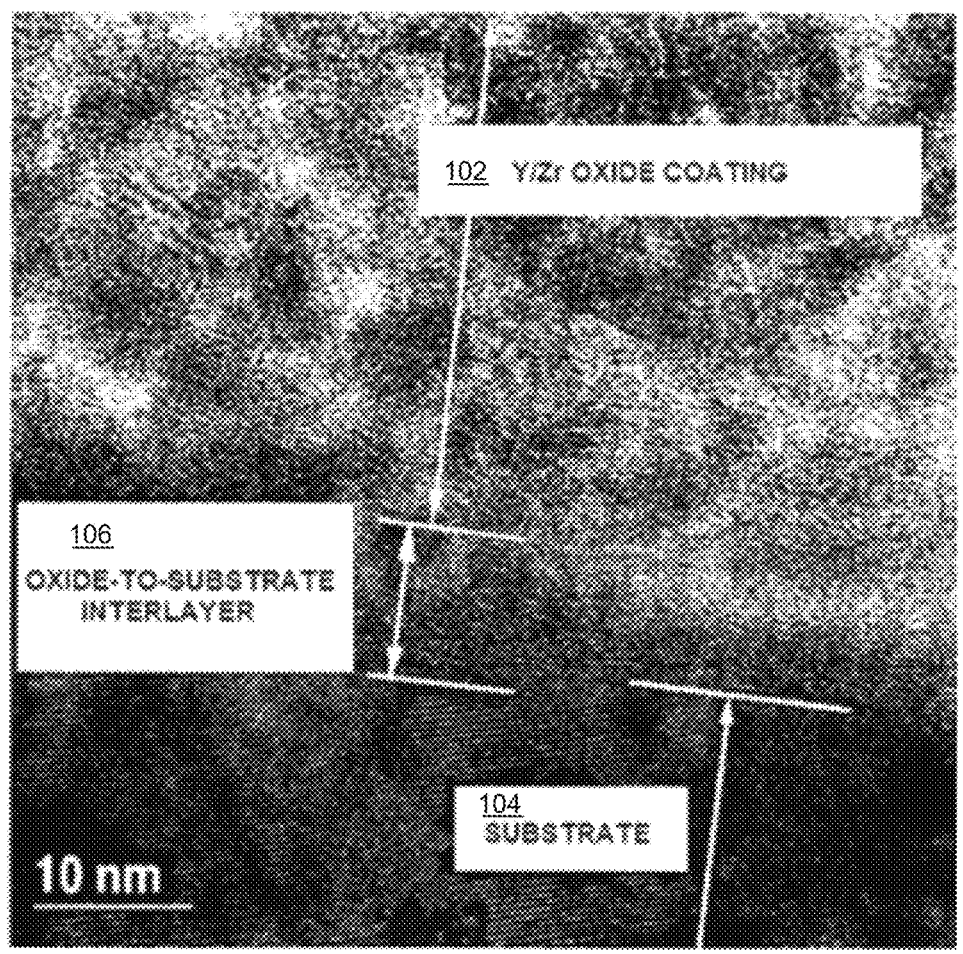
FIG. 1 is a micrograph at approximately two million× magnification that illustrates a thin film of yttria-stabilized zirconia ("YSZ": a material that can be used to produce ceramic electrolytes in solid oxide cells) with an interlayer (108) between the pure YSZ thin film (102) and the pure stainless steel (grade 304) of the substrate (104). The mixed YSZ-oxide & substrate interlayer (106) appears between the lower steel substrate layer (104) and the upper YSZ-oxide layer (102).

The present invention provides solid oxide cells, components thereof, and methods of making and using the same.
Electrolytes Some embodiments of the present invention include electrolytes and methods for making electrolytes having enhanced ionic conductivity ionic conductivity is the rate at which one or more ions move through a substance ionic conductivity generally depends upon temperature in most solid electrolytes, and is usually faster at higher temperature. In some cases, poor ionic conductivity at room temperature prevents economical use of certain fuel cell technologies. Accordingly, enhancing ionic conductivity can provide either more efficient solid oxide cell operation at a given temperature, or operation at a lower temperature that is thereby rendered efficient enough to be economically feasible.

Ionic conductivity can relate to any ionic conductivity, such as, for example, the conductivity of monoatomic, diatomic, and multiatomic ions; monovalent, divalent, trivalent, tetravalent, and other multivalent ions; cations; anions; solvated and partially-solvated ions, and combinations thereof. In some embodiments, ionic conductivity concerns the conductivity of $O^{2-}$. In other embodiments, ionic conductivity concerns the conductivity of $O^{2-}$, $H^+$, $H_3O^+$, $OH^-$, $NH_4^+$, $Li^+$, $Na^+$, $K^+$, $Mg^+$, $Ca^+$, $F^-$, $Cl^-$, $Br^-$, $I_3^-$, $I^-$, and combinations thereof. Ionic conductivity is often reported in units of 1/(ohms cm) or S/cm, where 1 S=1 A/V. In context of the present invention, ionic conductivity is enhanced if, in reference to a literature or experimental value of bulk ionic conductivity of the most-ionic conductive material in the metal oxide electrolyte, the ionic conductivity has increased by a statistically significant amount. In some embodiments the ionic conductivity has increased at least one order of magnitude, from about one order of magnitude to about two orders of magnitude, from about two orders of magnitude to about three orders of magnitude, from about three orders of magnitude to about four orders of magnitude, from about four orders of magnitude to about five orders of magnitude, from about five orders of magnitude to about six orders of magnitude, from about six orders of magnitude to about seven orders of magnitude, from about seven orders of magnitude to about eight orders of magnitude, from about eight orders of magnitude to about nine orders of magnitude, from about nine orders of magnitude to about ten orders of magnitude, or greater than about ten orders of magnitude.

Certain embodiments of the present invention relate to methods of enhancing ionic conductivity in a metal oxide electrolyte comprising a first material and a metal oxide comprising:
applying a metal compound to the first material; and
converting at least some of the metal compound to form the metal oxide;
wherein the first material and the metal oxide have an ionic conductivity greater than the bulk ionic conductivity of the first material and of the metal oxide. In those embodiments the first material may provide a substrate for the formation of the metal oxide or the first material and the metal compound are deposited simultaneously or sequentially on a substrate for the converting. Thus, the first material may be in any suitable physical form, from thin sheets or films to powders to nanobars, in some embodiments. When the first material is present in e powdered form, the first material can comprise particles having an average size or diameter of less than about 1 cm, or less than about 0.5 cm, in some embodiments. In other embodiments, the first material in powdered form has an average a size or diameter ranging from about 2 mm to about 0.5 cm, or from about 2 nm to about 10 nm, or from about 10 nm to about 50 nm from about 50 nm to about 100 nm, from about 100 nm to about 250 nm, from about 250 nm to about 500 nm, from about 500 nm to about 1 micron, from about 1 micron to about 5 microns, from about 5 microns to about 50 microns, from about 50 microns to about 100 microns, from about 100 microns to about 250 microns, from about 250 microns to about 500 microns from about 500 microns to about 1 mm, from about 1 mm to about 5 mm. The powder can comprise particles of any suitable shape, including but not limited to spheres, pyramids, cubes, polygons, irregular polygons, cylinders, nanobars, discs, flakes, irregularly-shaped solids, and combinations thereof. For shapes having a high aspect ratio the average size refers to the largest dimension of the shape, such as the length of a cylinder or the diameter of a disk. Some embodiments provide a first material in powder form comprising mica, and a metal oxide composing yttria-stabilized zirconia, gadolinium-doped ceria, alumina, or a combination thereof.

The first material in certain embodiments, can comprise, among other things, crystalline material, nanocrystalline material, metal oxides, nanobars mica flakes, thin sheets and combinations thereof. Crystalline material includes single crystals and material that has been formed epitaxially, such as by atomic layer deposition. In further embodiments, the first material is chosen from strontium titanate, titania, alumina, zirconia, yttria-stabilized zirconia, alumina-doped yttria-stabilized zirconia iron-doped zirconia magnesia, ceria, samarium-doped ceria, gadolinium-doped ceria, and combinations thereof. Additional embodiments provide the test material being chosen from alumina, titania, zirconia, yttria-stabilized zirconia, alumina-doped yttria-stabilized zirconia, iron-doped zirconia, magnesia, ceria samarium-doped ceria gadolinium-doped ceria, and combinations thereof.

In some embodiments, detection of a given material need not require crystallographic analysis. For example alumina-doped yttria-stabilized zirconia refers to oxide material comprising aluminum, yttrium, zirconium, and oxygen. Accordingly, detection of constituent elements signifies the indicated material. Elemental detection methods are widely known, and include, but are not limited to, flame emission spectroscopy, flame atomic absorption spectroscopy, electrothermal atomic absorption spectroscopy, inductively coupled plasma spectroscopy, direct-current plasma spectroscopy, atomic fluorescence spectroscopy, and laser-assisted flame ionization spectroscopy.

Mica appears as flakes, chunks, thin sheets or a combination thereof, in certain embodiments of the present invention. "Mica," as used in the present disclosure, refers to a family of readily-cleavable materials, synthetic or naturally-occurring, also known as phyllosilicates. Biotite, muscovite phlogopite, lepidolite, margarite, and glauconite, and combinations thereof, are types of mica that can be used.

Certain embodiments provide the first material in the form of a thin sheet. In some of those embodiments, the first material comprises at least one thin sheet. Thin sheets of material, such as, for example, mica, metal oxides, conductors, semiconductors, and insulators, can be used. Some embodiments employ thin sheets of MgO, $BaTiO_3$, NaCl, KCl, alone or in combination. Also, thin sheets are chosen from crystalline material such as slices of single crystal and epitaxial films grown on a substrate and optionally removed from that substrate. Other materials that can be used provide a thin sheet that can withstand the temperatures of processing and operation. In certain cases, that material is not electrically conductive, to avoid shorting out the solid oxide cell. In other cases, metal oxide or other electrical insulator is interposed between the conductive flat sheet and at least one electrode, to avoid snorting out the cell. For example the electrodes can comprise one or more alike or different metal oxide coatings formed by applying at least one metal compound to the electrode, and converting at least some of the at least one metal compound to at least one metal oxide.

In some embodiments, a thin sheet has a thickness ranging from about 1 micron to about 10 microns, from about 10 microns to about 50 microns, from about 50 microns to about 100 microns, from about 100 microns to about 200 microns, from about 200 microns to about 500 microns. In other embodiments, a thin sheet has a thickness of less than about 1 micron, or greater than about 500 microns. Optionally, one or more epoxies are used to fill in any defects or to seal a thin sheet.

When the first material comprises a thin sheet, in some embodiments, the first material is present in the solid oxide cell in a plurality of alike or different thin sheets. In certain embodiments, those thin sheets are oriented substantially parallel to each other, and substantially perpendicular to one or more electrodes. Thus, in the operation of the cell, ion diffusion through the metal oxide electrolyte occurs in a direction roughly parallel to the plane of the thin sheet, rather than through (or perpendicular to) the thin sheet. Thin sheets of ceramics, minerals, metal oxides, and combinations thereof can be used in metal oxide electrolytes in certain embodiments of the present invention.

Some embodiments of the present invention provide at least one metal oxide chosen from strontium titanate, titania, alumina, zirconia, yttria-stabilized zirconia, alumina-doped yttria-stabilized zirconia, iron-doped zirconia, magnesia, ceria, samarium-doped ceria, gadolinium-doped ceria, and combinations thereof. In other embodiments, the metal oxide is chosen from alumina, titania, zirconia, yttria-stabilized zirconia, alumina-doped yttria-stabilized zirconia, iron-doped zirconia, magnesia, ceria samarium-doped ceria, gadolinium-doped ceria, and combinations thereof.

In still further embodiments, the metal oxide electrolyte comprises a first material comprising strontium titanate, and a metal oxide comprising yttria-stabilized zirconia. In other embodiments, the first material comprises magnesia, and the metal oxide composes yttria-stabilized zirconia. Additional embodiments have a first material comprising titania, and a metal oxide composing yttria-stabilized zirconia. Yet other embodiments provide a first material comprising strontium titanate and a metal oxide comprising iron-doped zirconia. Certain embodiments include a first material comprising samarium-doped ceria, and a metal oxide comprising ceria.

Some additional embodiments provide yttria-stabilized zirconia comprising from about 10 mol % to about 20 mol % yttria, from about 12 mol % to about 18 mol % yttria, or from about 14 mol % to about 16 mol % yttria.

Applying one or more metal compounds to one or more materials can occur according to any suitable method. Dipping, spraying, brushing, mixing spin coating, and combinations thereof, among other methods, can be used. Then the metal compound is converted to form at least one metal oxide in the presence of the material, and optionally in the presence of a substrate. In certain embodiments, the metal compound is fully converted to a metal oxide. A metal compound composition comprises a metal-containing compound that can be at least partially converted to a metal oxide. In some embodiments, the metal compound composition composes a metal carboxylate, a metal alkoxide, a metal β-diketonate, or a combination thereof.

A metal carboxylate composes the metal salt of a carboxylic acid, e.g., a metal atom and a carboxylate moiety. In some embodiments of the present invention, a metal salt of a carboxylic acid comprises a transition metal salt. In other embodiments, a metal salt of a carboxylic acid comprises a rare earth metal salt. In a further embodiment metal carboxylate compositions comprise a plurality of metal salts of carboxylic acids. In one embodiment a plurality of metal salts composes a rare earth metal salt of a carboxylic acid and a transition metal salt of a carboxylic acid.

Metal carboxylates can be produced by a variety of methods known to one skilled in the art. Non-limiting examples of methods for producing the metal carboxylate are shown in the following reaction schemes.

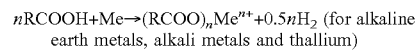
$n$RCOOH+Me→(RCOO)$_n$Me$^{n+}$+0.5$n$H$_2$ (for alkaline earth metals, alkali metals and thallium)

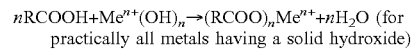
$n$RCOOH+Me$^{n+}$(OH)$_n$→(RCOO)$_n$Me$^{n+}$+$n$H$_2$O (for practically all metals having a solid hydroxide)

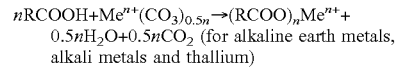
$n$RCOOH+Me$^{n+}$(CO$_3$)$_{0.5n}$→(RCOO)$_n$Me$^{n+}$+ 0.5$n$H$_2$O+0.5$n$CO$_2$ (for alkaline earth metals, alkali metals and thallium)

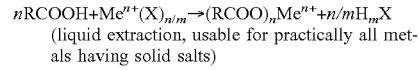
$n$RCOOH+Me$^{n+}$(X)$_{n/m}$→(RCOO)$_n$Me$^{n+}$+$n/m$H$_m$X (liquid extraction, usable for practically all metals having solid salts)

In the foregoing reaction schemes X is an anion having a negative charge m, such as, e.g., halide anion, sulfate anion, carbonate anion, phosphate anion, among others; n is a positive integer; and Me represents a metal atom. R in the foregoing reaction schemes can be chosen from a wide variety of radicals.

Suitable carboxylic acids for use in making metal carboxylates include, for example:

Monocarboxylic Acids:

Monocarboxylic acids where R is hydrogen or unbranched hydrocarbon radical, such as, for example, HCOOH-formic, $CH_3COOH$-acetic. $CH_3CH_2COOH$-propionic $CH_3CH_2CH_2COOH$ ($C_4H_8O_2$)-butyric, $C_5H_{10}O_2$-valeric, $C_6H_{12}O_2$-caproic, $C_7H_{14}$-enanthic; further, caprylic, pelargonic, undecanoic, dodecanoic, tridecylic, myristic, pentadecylic, palmitic, margaric, stearic, and nonadecylic acids.

Monocarboxylic acids where R is a branched hydrocarbon radical, such as, for example, $(CH_3)_2CHCOOH$-isobutyric, $(CH_3)_2CHCH_2COOH$-3-methylbutanoic, $(CH_3)_3CCOOH$-trimethylacetic, including VERSATIC 10 (trade name) which is a mixture of synthetic, saturated carboxylic acid isomers, derived from a highly-branched $C_{10}$ structure.

Monocarboxylic acids in which R is a branched or unbranched hydrocarbon radical containing one or more double bonds, such as for example, $CH_2=CHCOOH$-acrylic, $CH_3CH=CHCOOH$-crotonic, $CH_3(CH_2)_7CH=CH(CH_2)_7COOH$-oleic, $CH_3CH=CHCH=CHCOOH$-hexa-2,4-dienoic, $(CH_3)_2C=CHCH_2CH_2C(CH_3)=CHCOOH$-3,7-dimethyl-octa-2,6-dienoic, $CH_3(CH_2)_4CH=CHCH_2CH=CH(CH_2)_7COOH$-linoleic, further: angelic, tiglic, and elaidic acids;

Monocarboxylic acids in which R is a branched or unbranched hydrocarbon radical containing one or more triple bonds, such as, for example, $CH\equiv CCOOH$-propiolic, $CH_3C\equiv CCOOH$-tetrolic, $CH_3(CH_2)_4C\equiv CCOOH$-oct-2-ynoic, and stearolic acids;

Monocarboxylic acids in which R is a branched or unbranched hydrocarbon radical containing one or more double bonds and one or more triple bonds.

Monocarboxylic acids in which R is a branched or unbranched hydrocarbon radical containing one or more double bonds and one or more triple bonds and one or more aryl groups;

Monohydroxymonocarboxylic acids in which R is a branched or unbranched hydrocarbon radical that contains one hydroxyl substituents such as, for example, $HOCH_2COOH$-glycolic, $CH_3CHOHCOOH$-lactic, $C_6H_5CHOHCOOH$-amygdalic, and 2-hydroxybutyric acids;

Dihydroxymonocarboxylic acids in which R is a branched or unbranched hydrocarbon radical that contains two hydroxyl substituents, such as, for example, $(HO)_2CHCOOH$-2,2-dihydroxyacetic acid;

Dioxycarboxylic acids, in which R is a branched or unbranched hydrocarbon radical that contains two oxygen atoms each bonded to two adjacent carbon atoms, such as, for example, $C_6H_3(OH)_2COOH$-dihydroxy benzoic, $C_6H_2(CH_3)(OH)_2COOH$-orsellinic; further: caffeic, and piperic acids;

Aldehyde-carboxylic adds in which is a branched or unbranched hydrocarbon radical that contains one aldehyde group, such as, for example, CHOCOOH-glyoxalic acid;

Keto-carboxylic acids in which R is a branched or unbranched hydrocarbon radical that contains one ketone group, such as, for example, $CH_3COCOOH$-pyruvic, $CH_3COCH_2COOH$-acetoacetic, and $CH_3COCH_2CH_2COOH$-levulinic acids.

Monoaromatic carboxylic acids, in which R is a branched or unbranched hydrocarbon radical that contains one aryl substituent, such as, for example, $C_6H_5COOH$-benzoic, $C_6H_5CH_2COOH$-phenylacetic, $C_6H_5CH(CH_3)COOH$-2-phenylpropanoic, $C_6H_5CH=CHCOOH$-3-phenylacrylic, and $C_6H_5C\equiv CCOOH$-3-phenyl-propiolic acids;

Multicarboxylic Acids:

Saturated dicarboxylic acids, in which R is a branched or unbranched saturated hydrocarbon radical that contains one carboxylic acid group, such as, for example, HOOC—COOH-oxalic, $HOOC—CH_2—COOH$-malonic, $HOOC—(CH_2)_2—COOH$-succinic, $HOOC—(CH_2)_3—COOH$-glutaric, $HOOC—(CH_2)_4—COOH$-adipic; further: pimelic, suberic, azelaic, and sebacic acids;

Unsaturated dicarboxylic acids, in which R is a branched or unbranched hydrocarbon radical that contains one carboxylic acid group and a carbon-carbon multiple bond, such as, for example, HOOC—CH=CH—COOH-fumaric; further: maleic, citraconic, mesaconic, and itaconic acids;

Polybasic aromatic carboxylic acids, in which R is a branched or unbranched hydrocarbon radical that contains a aryl group and a carboxylic acid group, such as, for example, $C_6H_4(COOH)_2$-phthalic (isophthalic, terephthalic), and $C_6H_3(COOH)_3$-benzyl-tri-carboxylic acids;

Polybasic saturated carboxylic acids, in which R is a branched or unbranched hydrocarbon radical that contains a carboxylic acid group, such as, for example, ethylene diamine N,N'-diacetic acid, and ethylene diamine tetraacetic acid (EDTA);

Polybasic Oxyacids:

Polybasic oxyacids, in which R is a branched or unbranched hydrocarbon radical containing a hydroxyl substituent and a carboxylic acid group, such as, for example, HOOC—CHOH—COOH-tartronic, $HOOC—CHOH—CH_2—COOH$-malic, $HOOC—C(OH)=CH—COOH$-oxaloacetic, HOOC—CHOH—CHOH—COOH-tartaric, and $HOOC—CH_2—C(OH)COOH—CH_2COOH$-citric acids.

A metal compound composition, in some embodiments of the present invention, comprises a solution of carboxylic acid salts of one or more metals ("metal carboxylate"). A liquid metal carboxylate composition can comprise a single metal, to form a single metal carboxylate, or a mixture of metals, to form a corresponding mixture of metal carboxylates. In addition, a liquid metal carboxylate composition can contain different carboxylate moieties. In some embodiments, a liquid metal carboxylate composition contains a mixture of metals, as these compositions form mixed oxides having various properties.

Solvent used in the production of liquid metal carboxylate compositions, in some embodiments, comprise an excess of the liquid carboxylic acid which was used to form the metal carboxylate salt. In other embodiments, a solvent comprises another carboxylic acid, or a solution of a carboxylic acid in another solvent, including, but not limited to, organic solvents such as benzene, toluene, chloroform, dichloromethane, or combinations thereof.

Carboxylic acids suitable for use generating liquid metal carboxylate compositions, in some embodiments, are those which: (1) can form a metal carboxylate, where the metal carboxylate is soluble in excess acid or another solvent; and (2) can be vaporized in a temperature range that overlaps with the oxide conversion temperature range.

In some embodiments, a carboxylic acid has a formula R—COOH, where R is alkyl, alkenyl, alkynyl or aryl.

In some embodiments, the monocarboxylic acid comprises one or more carboxylic acids having the formula I below:

$$R^o—C(R'')(R')—COOH \quad (I)$$

wherein:

R° is selected from H or $C_1$ to $C_{24}$ alkyl groups; and

R' and R" are each independently selected from H and $C_1$ to $C_{24}$ alkyl groups;

wherein the alkyl groups of R°, R', and R" are optionally and independently substituted with one or more substituents, which are alike or different chosen from hydroxy alkoxy, amino, and aryl radicals, and halogen atoms.

The term alkyl, as used herein, refers to a saturated straight, branched, or cyclic hydrocarbon or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl, heptyl, octyl, nonyl, and decyl.

The term alkoxy, as used herein, refers to a saturated straight, branched, or cyclic hydrocarbon, or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl 2,2-dimethylbutyl, 2,3-dimethylbutyl, heptyl, octyl, nonyl, and decyl, in which the hydrocarbon contains a single-bonded oxygen atom that can bond to or is bonded to another atom or molecule.

The terms alkenyl and alkynyl as used herein, refer to a straight, branched, or cyclic hydrocarbon. Including $C_1$ to $C_{24}$, with a double or triple bond, respectively.

Alkyl, alkenyl, alkoxy, and alkynyl radicals are unsubstituted or substituted with one or more alike or different substituents independently chosen from halogen atoms, hydroxy, alkoxy, amino, aryl, and heteroaryl radicals.

Moreover, the term aryl or aromatic, as used herein, refers to a monocyclic or bicyclic hydrocarbon ring molecule having conjugated double bonds about the ring. In some embodiments, the ring molecule has 5- to 12-members, but is not limited thereto. The ring may be unsubstituted or substituted having one or more alike or different independently-chosen substituents, wherein the substituents are chosen from alkyl, alkenyl, alkynyl, alkoxy, hydroxyl, and amino radicals, and halogen atoms. Aryl includes, for example, unsubstituted or substituted phenyl and unsubstituted or substituted naphthyl.

The term heteroaryl as used herein refers to a monocyclic or bicyclic aromatic hydrocarbon ring molecule having a heteroatom chosen from O, N, P, and S as a member of the ring, and the ring is unsubstituted or substituted with one or more alike or different substituents independently chosen from alkyl, alkenyl, alkynyl, hydroxyl, alkoxy, amino, alkylamino, dialkylamino, thiol, alkylthio, =O, =NH, =PH, =S, and halogen atoms. In some embodiments, the ring molecule has 5- to 12-members, but is not limited thereto.

The alpha branched carboxylic acids, in some embodiments, nave an average molecular weight ranging from about 130 to 420 g/mol or from about 220 to 270 g/mol. The carboxylic acid may also be a mixture of tertiary and quaternary carboxylic acids of formula I. VIK acids can be used as well. See U.S. Pat. No. 5,952,759, at col. 6, II. 12-51, which patent is incorporated herein by reference in its entirety.

In some embodiments, one or more metal carboxylates can be synthesized by contacting at least one metal hailde with at least one carboxylic acid in the substantial absence of water. In other embodiments, the contacting occurs in the substantial absence of a carboxylic anhydride, yet in specific embodiments at least one carboxylic anhydride is present. In still other embodiments, the contacting occurs in the substantial absence of a catalyst; however, particular embodiments provide at least one catalyst. For example, silicon tetrachloride, aluminum trichloride, titanium tetrachloride, titanium tetrabromide, or a combination of two or more thereof can be mixed into 2-ethylbexanoic acid, glacial acetic acid, or another carboxylic acid or a combination thereof in the substantial absence of water with stirring to produce the corresponding metal carboxylate or combination thereof. Carboxylic anhydrides and/or catalysts can be excluded, or are optionally present. In some embodiments, the carboxylic acid is present in excess in other embodiments, the carboxylic acid is present in a stoichiometric ratio to the at least one metal halide. Certain embodiments provide the at least one carboxylic acid in a stoichiometric ratio with the at least one metal halide of about 1:1, about 2:1, about 3:1, or about 4:1. The contacting of the at least one metal halide with at least one carboxylic acid can occur under any suitable conditions. For example, the contacting optionally can be accompanied by heating, partial vacuum, and the like.

Either a single carboxylic acid or a mixture of carboxylic acids can be used to form the liquid metal carboxylate. In some embodiments, a mixture of carboxylic acids contains 2-ethylhexanoic acid wherein R° is H, R" is $C_2H_5$ and R' is $C_4H_9$, in the formula (I) above. The use of a mixture of carboxylates can provide several advantages. In one aspect, the mixture has a broader evaporation temperature range, making it more likely that the evaporation, temperature of the and mixture will overlap the metal carboxylate decomposition temperature, allowing the formation of a metal oxide coating. Moreover, the possibility of using a mixture of carboxylates avoids the need and expense of purifying an individual carboxylic acid.

Other metal compounds can be used to form metal oxides in accordance with the present invention. Such metal compounds can be used alone or in combination, or in combination with one or more metal carboxylates. Metal compounds other than carbonates and those mentioned elsewhere include metal alkoxides and metal β-adiketonates.

Metal alkoxides suitable for use in the present invention include a metal atom and at least one alkoxide radical —OR² bonded to the metal atom. Such metal alkoxides include those of formula II:

$$M(OR^2)_z \qquad (II)$$

in which M is a metal atom of valence z+;

z is a positive integer, such as, for example, 1, 2, 3, 4, 5, 6, 7, and 8;

$R^2$ can be alike or different and are independently chosen from unsubstituted and substituted alkyl, unsubstituted and substituted alkenyl, unsubstituted and substituted alkynyl, unsubstituted and substituted heteroaryl, and unsubstituted and substituted aryl radicals.

wherein substituted alkyl, alkenyl, alkynyl, heteroaryl, and aryl radicals are substituted with one or more alike or different substituents independently chosen from halogen, hydroxy, alkoxy, amino, heteroaryl, and aryl radicals In some embodiments, z is chosen from 2, 3, and 4.

Metal alkoxides are available from Alfa-Aesar and Gelest, Inc., of Morrisville, Pa. Lanthanoid alkoxides such as those of Ce, Nd, Eu, Dy, and Er are sold by Kojundo Chemical Co., Saitama, Japan, as well as alkoxides of Al, Zr, and Hf, among others. See. e.g., http://www.kojundo.co.jp/English/Guide/material/lanthagen.html. Examples of metal alkoxides useful in embodiments of the present invention include methoxides, ethoxides, propoxides, isopropoxides, and butoxides and isomers thereof. The alkoxide substituents on a give metal atom are the same or different. Thus, for example, metal dimethoxide diethoxide, metal methoxide diisopropoxide t-butoxide, and similar metal alkoxides can be used. Suitable alkoxide substituents also may be chosen from.
1. Aliphatic series alcohols from methyl to dodecyl including branched and isostructured.
2. Aromatic series alcohols benzyl alcohol —$C_6H_5CH_2OH$; phenyl-ethyl alcohol —$C_8H_{10}O$; phenyl-propyl alcohol —$C_9H_{12}O$, and so on.

Metal alkoxides useful in the present invention can be made according to many suitable methods. One method includes converting the metal halide to the metal alkoxide in the presence of the alcohol and its corresponding base. For example:

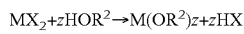

in which M, $R^2$, and z are as defined above for formula II, and X is a halide anion.

Metal β-diketonates suitable for use in the present invention contain a metal atom and a β-diketone of formula III as a ligand:

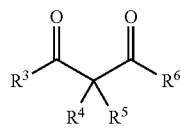

(III)

in which
$R^3$, $R^4$, $R^5$, and $R^6$ are alike or different, and are independently chosen from hydrogen, unsubstituted and substituted alkyl, unsubstituted and substituted alkoxy, unsubstituted and substituted alkenyl, unsubstituted and substituted alkynyl, unsubstituted and substituted heteroaryl, unsubstituted and substituted aryl carboxylic acid groups, ester groups having unsubstituted and substituted alkyl, and combinations thereof,
wherein substituted alkyl, alkoxy, alkenyl, alkynyl, heteroaryl, and aryl radicals are substituted with one or more alike or different substituents independently chosen from halogen atoms, hydroxy, alkoxyl, amino, heteroaryl, and aryl radicals.

It is understood that the β-diketone of formula III may assume different isomeric and electronic configurations before and while chelated to the metal atom. For example, the free β-diketone may exhibit enolate isomerism. Also the β-diketone may not retain strict carbon-oxygen double bonds when the molecule is bound to the metal atom.

Examples of β-diketones useful in embodiments of the present invention include acetylacetone, trifluoroacetylacetone, hexafluoroacetylacetone, 2,2,6,6-tetramethyl-3,5-heptanedione, 6,6,7,7,8,8,8-heptafluoro-2,2-dimethyl-3,5-octanedione, ethyl acetoacetate, 2-methoxyethyl acetoacetate, benzoyltrifluoroacetone, pivaloyltrifluoroacetone, benzoyl-pyruvic acid, and methyl-2,4-dioxo-4-phenylbutanoate.

Other ligands are possible on the metal β-diketonates useful in the present invention, such as, for example, alkoxides such as —$OR^2$ as defined above, and dienyl radicals such as, for example, 1,5-cyclooctadiene and norbomadiene. Metal β-diketonates useful in the present invention can be made according to any suitable method. β-diketones are well known as chelating agents for metals, facilitating synthesis of the diketonate from readily available metal salts;

Metal β-diketonates are available from Alfa-Aesar and Gelest, Inc. Also, Strem Chemicals, Inc. of Newburyport, Mass., sells a wide variety of metal β-diketonates on the internet at
http://www.strem.com/code/template.ghc?direct=cvdindex.

In some embodiments, a metal compound composition contains one metal compound as its major component and one or more additional metal compounds which may function as stabilizing additives. Stabilizing additives, in some embodiments, comprise trivalent metal compounds. Trivalent metal compounds include, but are not limited to, chromium, iron, manganese and nickel carboxylates. A metal compound composition, in some embodiments, composes both cerium and chromium carboxylates.

In some embodiments, the amount of metal forming the major component of the metal compound composition ranges from about 65 weight percent to about 97 weight percent or from about 80 weight percent to about 87 weight percent of the total metal in the compound composition. In other embodiments, the amount of metal forming the major component of the metal compound composition ranges from about 90 weight percent to about 97 weight percent of the total metal present in the compound composition. In a further embodiment, the amount of metal forming the major component of the metal compound composition is less than about 85 weight percent or greater than about 97 weight percent of the total metal present in the compound composition.

In some embodiments, metal compounds operable to function as stabilizing additives are present in amounts such that the total amount of the metal in metal compounds which are the stabilizing additives is at least 3% by weight of the total metal so the liquid metal compound composition.

The amount of metal in a liquid metal compound composition, according to some embodiments, ranges from about 20 to about 150 grains of metal per kilogram of liquid metal compound composition. In other embodiments the amount of metal in a liquid metal compound composition ranges from about 30 to about 50 grains of metal per kilogram of liquid metal compound composition. In a further embodiment, a liquid metal compound composition comprises from about 30 to about 40 grains of metal per kg of composition. In one embodiment, a metal amount is less than about 20 grains of metal per kilogram of liquid metal compound or greater than 150 grains of metal per kilogram of liquid metal compound.

Liquid metal compound compositions, in some embodiments of solid oxide cell production methods, further comprise one or more catalytic materials. Catalytic materials, in such embodiments, compose transition metals including, but not limited to, platinum, palladium, rhodium, nickel, cerium, gold, silver, zinc, lead, ruthenium, rhenium, or mixtures thereof. Catalytic materials, in some embodiments, are present in liquid metal compound compositions in an amount ranging from about 0.5 weight percent to about 10 weight percent of the composition. In further embodiments, one or more catalytic materials are present in an amount of less than about 0.5 weight percent of the composition. In still further embodiments, one or more catalytic materials are present in an amount of greater than about 10 weight percent of the composition. In certain embodiments, the catalytic material is present in the liquid metal compound composition in the form of a metal compound. In certain other embodiments, the catalytic material is present in the form of a metal.

In other embodiments a liquid metal compound composition further composes nanoparticles operable to alter the pore structure and porosity of the metal oxide resulting from the conversion of the liquid metal compound composition. Nanoparticles, in some embodiments comprise metal oxide nanoparticles. Nanoparticles, in some embodiments, are present in liquid metal compound compositions in an amount ranging from about 0.5 percent by volume to about 30 percent by volume of the liquid metal compound composition. In another embodiment, nanoparticles are present in the liquid metal compound composition in an amount ranging from about 5 percent by volume to about 15 percent by volume of the liquid metal compound composition.

In addition to liquids, metal compound compositions, in some embodiments of the present invention, comprise solid metal compound compositions, vapor metal compound compositions, or combinations thereof. In one embodiment, a solid metal compound composition comprises one or more metal compound powders. In another embodiment, a vapor metal compound composition composes a gas phase metal compound operable to condense on a substrate prior to conversion to a metal oxide. In some embodiments, the substrate is cooled to enhance condensation of the vapor phase metal compound composition. In one embodiment for example, a substrate such as a steel electrode substrate is placed in a vacuum chamber, and the chamber is evacuated. Vapor of one or more metal compounds, such as cerium (IV) 2-hexanoate, enters the vacuum chamber and deposits on the steel substrate. Subsequent to deposition, the metal compound is exposed to conditions operable to convert the metal compound to a metal oxide. In a further embodiment, a metal compound composition comprises gels chosen from suitable gels including, but not limited to, sol-gels, hydrogels, and combinations thereof.

Applying a metal compound composition to a substrate can be accomplished by any suitable method, such as those known to one of skill in the art. In one embodiment, the substrate is dipped into the liquid metal compound composition. In another embodiment, a swab, sponge, dropper, pipette, spray, brush or other applicator is used to apply the liquid metal compound composition to the substrate. In some embodiments, a vapor phase metal compound composition is condensed on the substrate. In other embodiments, lithographic methods can be used to apply the metal compound composition to the substrate.

A metal compound composition, in some embodiments, is applied to the substrate at a temperature less than about 25° C. In other embodiments, a metal compound composition is applied to the substrate at a temperature less than about 200° C., less than about 150° C., less than about 100° C., or less than about 50° C. In a further embodiment, a metal compound composition is applied to the substrate at room temperature. An additional embodiment provides a metal compound composition applied at less than about room temperature.

A substrate onto which the at least one metal compound and optionally one or more additional materials is applied is not limited. In some embodiments, the substrate is an electrode, while in other embodiments, the substrate is a thin sheet. In still other embodiments, a substrate is used only for forming the metal oxide electrolyte. After the metal compound is converted to the metal oxide, the substrate in such embodiments is removed.

A substrate, in some embodiments, is pretreated prior to application of the metal compound composition. In one embodiment, for example, the substrate can be etched according to known methods, for example with an acid wash comprising nitric acid, sulphuric acid, hydrochloric acid, phosphoric acid, or a combination thereof, or with a base wash composing sodium hydroxide or potassium hydroxide, for example. In another embodiment, the substrate is polished, with or without the aid of one or more chemical etching agents, abrasives, and polishing agents, to make the surface either rougher or smoother in a further embodiment, the substrate is pretreated such as by carburizing, nitriding, plating, or anodizing.

Following application, the metal compound composition is at least partially convened to a metal oxide. In some embodiments, the metal compound composition is fully converted to a metal oxide.

Converting a metal compound composition comprising a metal salt of a carboxylic acid, according to some embodiments of the present invention, comprises exposing the metal compound composition to an environment operable to convert the metal salt to a metal oxide. Environments operable to convert metal compounds to metal oxides, in some embodiments, provide conditions sufficient to vaporize and/or decompose the compound moieties and precipitate metal oxide formation. In one embodiment, an environment operable to convert metal compounds to metal oxides comprises a heated environment. A metal salt of a carboxylic acid, for example, can be exposed to an environment heated to a temperature operable to convert the carboxylic acid and induce formation of the metal oxide. In some embodiments, the environment is heated to a temperature greater than about 200° C. In other embodiments the environment is heated to a temperature greater then about 400° C. In certain embodiments, the environment heated to a temperature up to about 425° C. or up to about 450° C. In additional embodiments, the environment is heated to a temperature ranging from about 400° C. to about 650° C. In a further embodiment, the environment is heated to a temperature ranging from about 400° C. to about 550° C.

The rate at which the environment is heated to effect the conversion of the at least one metal compound to the at least one metal oxide is not limited. In some embodiments, the heating rate is less than about 7° C./minute. In other embodiments, the heating rate is equal to about 7° C./minute. In still other embodiments, the heating rate is greater than about 7° C./minute. The heating rate, according to certain iterations of the present invention, is equal to the heating rate of the oven in which the conversion takes place. Particular embodiments provide a heating rate that is as fast as the conditions and equipment allow.

In some embodiments, the metal oxide penetrates into the substrate to a depth ranging from about 10 nm to about 100 nm or from about 20 nm to about 80 nm. In other embodiments, the metal oxide penetrates into the substrate to a depth ranging from about 30 nm to about 60 nm or from about 40 nm to about 50 nm. Converting the metal compound on the substrate to a metal oxide, in some embodiments, produces a transition layer composing metal oxide and substrate material, in some embodiments. In other embodiments the metal oxide does not penetrate into the substrate and an abrupt interface exists between the metal oxide and the substrate.

Moreover, exposing metal compound compositions to environments operable to convert the compositions to metal oxides, as provided herein, eliminates or reduces the need for sintering to produce metal oxides. By eliminating sintering, solid oxide cell production methods of the present invention gam several advantages One advantage is that the lower temperatures of some methods of the present invention do not induce grain growth or other degradative processes in various components of the solid oxide cell during production. Another advantage is that the compound compositions permit tailoring of individual metal oxide layers in the construction of electrolytes and electrodes. Methods of the present invention, for example, permit one metal oxide layer of an electrolyte or electrode to have completely different compositional and/or physical parameters in comparison to an adjacent metal oxide layer, in some embodiments. Such control over the construction of electrolytes and electrodes of solid oxide cells is extremely difficult and, in many cases, not possible with present sintering techniques. In other embodiments, for example one material can be prepared with conventional techniques such as sintering or epitaxial growth, while a metal oxide can be formed on that material without the need for sintering.

The conversion environment, for various embodiments of the present invention can be any suitable environment, and the conversion can be precipitated by any suitable means. In some embodiments of the present invention, the substrate is heated; in others, the atmosphere about the metal compound composition is heated; in still others, the metal compound composition is heated. In further embodiments, a substrate having a metal compound composition deposited thereon can be heated in an oven, or exposed to heated gas. The conversion environment may also be created using induction heating through means familiar to those skilled in the art of induction heating. Alternatively the conversion environment may be provided using a laser applied to the surface area for sufficient time to allow at least some of the metal compounds to convert to metal oxides. In other applications, the conversion environment may be created using an infra-red light source which can reach sufficient temperatures to convert at least some of the metal compounds to metal oxides. Some embodiments may employ a microwave emission device to cause at least some of the metal compound to convert. Other embodiments provide a plasma to heat the metal compound. In the case of induction heating, microwave heating, lasers, plasmas, and other heating methods that can produce the necessary heat levels in a short time, for example, within seconds, 1 minute, 10 minutes, 20 minutes, 30 minutes, 40 minutes, or one hour.

Further embodiments of the present invention relate to methods for forming a metal oxide electrolyte, comprising: applying a metal compound to a first material in nanobar form; and
converting at least some of the metal compound to form a metal oxide, thereby forming the metal oxide electrolyte; wherein the metal oxide electrolyte has an ionic conductivity greater than the bulk ionic conductivity of the first material and of the metal oxide. Still other embodiments relate to electrolytes so formed, wherein the nanobars conform to an orientation. That means that the greater dimension (length) of at least a portion of the nanobars substantially align in the same direction. Conforming to an orientation is caused, in some embodiments, by applying an orienting force before, during, or both before and during the converting of the metal compound to the metal oxide. Certain embodiments supply an orienting force after the converting as well. Orienting forces are not limited, and can be chosen from brushing spin coating, one or more magnetic fields, one or more electric fields, and combinations thereof. In some embodiments, the magnetic field is chosen from static magnetic fields, variable magnetic fields, uniform magnetic fields, non-uniform magnetic fields, and combinations thereof.

Some devices for applying suitable magnetic fields appear, for example, U.S. Pat. No. 7,161,124 B2 to Kisner at al., which is incorporated by reference herein in its entirety. Devices for applying suitable magnetic fields optionally provide one or more of heating, cooling, vacuum, fluid flushing, and manipulating means to the substrate being coated. Some embodiments provide a quartz vessel for holding one or more components to be coated in a magnetic field. Such a vessel, in some embodiments, contains one or more means for holding components so that evacuating, applying a magnetic field, heating, and cooling do not dislodge the components. Such means for holding components include quarts structures in the vessel that immobilize the components being coated. Care should be taken so that components are not permitted to accelerate by the application of a large magnetic field. Quartz and similar materials that are not affected by strong magnetic fields or higher temperatures are suitable for some embodiments.

The magnetic field can be any suitable strength. In some embodiments, the magnetic field is less than one Tesla. In still further embodiments, the magneto field ranges from about 1 Tesla to about 2 Tesla, from about 2 Tesla to about 4 Tesla from about 4 Tesla to about 6 Tesla, from about 6 Tesla to about 8 Tesla, from about 8 Tesla to about 10 Tesla, or greater than about 10 Tesla.

In other embodiments, the electric field is chosen from static electric fields, variable electric fields, uniform electric fields, non-uniform electric fields, and combinations thereof. For example, two large conductive plates arranged like a parallel plate capacitor can provide a substantially uniform electric field. Into the field is placed a substrate comprising at least one metal compound and at least one nanobar, in some embodiments, and the temperature is raised to effect conversion of the metal compound to metal oxide while under the effect of the electric field. Optionally, the electrodes that will form the cell can be charged to create an electric field. Or a corona poling arrangement can be made, in which a charged needle provides an electric field and scans across the substrate having thereon at least one metal oxide and at least one kind of nanobar. Scanning with the needle is a means for converting the metal compound into metal oxide, such as, for example, one or more laser diodes or a mirror directing a laser beam to the region where the electric field is strongest. In that manner, the conversion of the metal compound to form the metal oxide would lock in the orientation of the nanobars provided by the charged needle.

To establish an electric field a device capable of applying and maintaining a high voltage difference across two electrodes is needed. The Slaughter Company, of Lake Forest, Ill. (www.hipot.com) offers several "hipot" or high potential instruments providing up to 6000 V AC or DC. In certain embodiments, at least one metal compound and at least one nanobar are applied to an electrode to be used in a cell and another electrode to be used in the cell is positioned substantially parallel to the first electrode. Optionally, the second electrode is close enough to touch the at least one metal compound; but care is taken to avoid shorting the two electrodes. An electric potential is applied across the two electrodes and the resulting field orients at least a portion of the nanobars, and the metal compound is heated to convert into the metal oxide, such as, for example by an oven containing the two electrodes.

Further embodiments provide a nanobar having one or more alike or different derivatives. For example, a nanobar can be chemically functionalized at the bar end, at the sidewall, or a combination thereof. Tube end functionalization, in certain embodiments, facilitates the addition of one or more ionic or non-ionic species that can assist in orienting the nanobar in an electric or magnetic field. Tube end and sidewall functionalization can be obtained, for example, by reacting carbon nanotubes with diazonium species as described in U.S. Pat. No. 7,250,147, which patent is incorporated herein by reference in its entirety. Accordingly, in one embodiment, a benzenediazonium tetrafluoroborate salt para-substituted with a chosen functional group is attached to single-wall carbon nanotubes by holding a bucky paper working electrode comprising the nanotubes at −1.0 V vs Ag/AgNO$_3$ in a solution of the salt for 30 minutes. The nanotubes so functionalized are then mixed with metal compound, applied to a substrate, oriented in a magnetic or electric field, or by brushing or spin-coating, and the metal compound is converted to form the metal oxide about the functionalized nanotube.

In a further embodiment, 4-hydroxycarbonylphenyldiazonium tetrafluoroborate functionalizes single-wall carbon nanotubes in accordance with the '147 patent. Then, one or more metal ions are added to the carboxylate groups, for example, by rinsing with mild basic solution to deprotonate the carboxylase groups, and then one or more alike or different metal salts are introduced. The nanotubes functionalized with metal carboxylates are dispersed on a substrate optionally with one or more alike or different metal compounds, and the environment is heated to form one or more metal oxides from the metal sons on the nanotubes and optional metal compounds. In some embodiments, the nanotubes are oriented by brushing, spin coating, or by applying a magnetic or electric field, or by a combination of any of the foregoing. In certain embodiments, oriented domains of metal oxide are formed. In other embodiments, an electrolyte comprising oriented domains of metal oxide appear wherein the electrolyte has an ionic conductivity greater than the bulk ionic conductivity of the metal oxide.

Nanobars, such as carbon nanotubes can be functionalized for example by reacting with fluorine gas, and optionally further reacting with one or more nucleophilic species as set forth to U.S. Patent Application Publication No. US2002/0004028, which is incorporated herein by reference in its entirety, U.S. Patent Application Publication No. US2005/0089684 discloses the deposition of inorganic oxides such as silica on carbon nanotubes optionally functionalized for example with hydroxyl groups. Once the nanotubes are at least partially coated with silica the coating process is stopped and the nanotubes can be deposited on a substrate, for example, for microelectronic device fabrication. The '684 publication is incorporated herein by reference in its entirety. US Patent Application Publication No. 2008/0233040, which is also incorporated herein by reference in its entirety, describes functionalizing the silica coating of silica-coated nanotubes. K. Hernadi et al. "Synthesis of MWNT-based Composite Materials with inorganic Coating," Acta Mater., 51 (2003) 1447, discloses forming alumina, silica, and titania on multi-walled carbon nanotubes using metal alkoxide compounds. The Hernadi article is incorporated by reference herein in its entirety.

Some embodiments of the present invention provide a method for making a metal oxide electrolyte, comprising applying a nanobar functionalized with a metal compound to a substrate, optionally orienting the nanobar, and converting the metal compound to a metal oxide, thereby forming the metal oxide electrolyte; wherein the metal oxide electrolyte has an ionic conductivity greater than the bulk ionic conductivity of the metal oxide. Further embodiments relate to the metal oxide electrolyte so made, while even further embodiments relate to a solid oxide cell comprising a metal oxide electrolyte so made. Optionally a metal compound is applied to the substrate before, during, and/or after the applying of the nanobar, and that metal compound can be the same or different from the metal compound functionalizing the nanobar. In certain embodiments, the metal oxide electrolyte comprises the nanobar. In other embodiments, the nanobar does not appear, in some cases because the conversion conditions have destroyed the nanobar. Further embodiments provide the metal oxide in oriented domains.

In another embodiment, nanobars such as inorganic nanorods or carbon nanotubes chosen from single wall nanotubes, multiwall nanotubes and combinations thereof are contacted with one or more alike or different metal compounds, applied to a substrate, optionally orienting the nanobars, and converting at least some of the metal compound to form metal oxide, thereby forming a metal oxide electrolyte having an ionic conductivity greater than the bulk ionic conductivity of the metal oxide. In some embodiments, the applying action orients the nanobars, such as brushing or spin coating. In other embodiments, one or more separate orienting steps are taken, such as, for example, brushing, spin costing, exposing the nanobars to an electric field or a magnetic field, or a combination thereof. In certain cases, the nanobar remains in the metal oxide electrolyte, while in other cases, the nanobar is partially or completely absent, for example due to reaction, decomposition, sublimation, or the like. Additional embodiments provide pairs of metal compounds in any ratio chosen from yttrium and zirconium, samarium and cerium, barium and titanium, strontium and titanium, and combinations thereof.

In yet another embodiment a metal compound is applied to mica flakes to form a mixture, and the mixture is applied to a planar electrode. Another planar electrode is placed over the mixture on the first electrode, an electric field established by the two electrodes, and the metal compound is converted to form the metal oxide. Optionally, the mica flakes are preselected for susceptibility to orient in an electric field. One method to preselect involves sorting a collection of mica flakes in an electric field, whereby those mica flakes that are affected by the electric field are separated from those mica flakes that show little or no effect from the electric field, in another embodiment, mica flakes are pretreated, such as, for example, by contacting with acid or with base, and then optionally preselected for susceptibility to orient in an electric field. In still other embodiments, mica flakes are preselected for susceptibility to orient in a magnetic field, optionally following contact with acid or with base. Without wishing to be bound by theory, it is believed that contact with acid or with base modifies the surface properties such as surface charge, allowing the mica flake to orient in an electric field or magnetic field.

Accordingly, further embodiments provide applying an orienting force to a first material in powder form before, during, or before and during the converting of the metal compound to the metal oxide. In some embodiments, the orienting force is chosen from magnetic fields, electric fields, and combinations thereof.

Further embodiments provide sequential formation of two or more metal oxides to form a metal oxide electrolyte. For example, a first metal compound is applied to a substrate such as an electrode, and converted to a first metal oxide Depending on the amount of metal compound and the manner of application, the resulting first metal oxide is porous, in some embodiments. Then, a second metal compound is applied to the surface having the first metal oxide, and converted to a second metal oxide. Successive domains of first metal oxide and second metal oxide are formed on the surface by repeatedly applying and converting the respective metal compounds. In that way, a metal oxide electrolyte can be built on the substrate so that multiple interfaces between the first metal oxide and second metal oxide form. Depending on the amount, or if present in a composition, the concentration, of the metal compounds the resulting metal oxide domains can have pores, voids, or discontinuities. Those defects can allow the penetration of subsequently applied metal compound into the metal oxide, and give rise to interfaces between the oxides that run roughly perpendicularly from the surface of the substrate. Without wishing to be bound by theory those vertical interfaces can give use to crystal structure defects between the two oxides and enhance ionic conductivity. In some embodiments, a superlattice can be formed of alternating interpenetrating layers of metal oxides.

Accordingly, some embodiments provide a method for forming a metal oxide electrolyte, comprising:
applying a first metal compound to a substrate;
converting at least some of the first metal compound to form a first metal oxide on the substrate; applying a second metal compound to the substrate composing the first metal oxide; and
converting at least some of the second metal compound to form a second metal oxide on the substrate composing the first metal oxide,
thereby forming the metal oxide electrolyte;
wherein the metal oxide electrolyte has an some conductivity greater than the bulk ionic conductivity of the first metal oxide and of the second metal oxide. Further embodiments provide applying additional first metal compound to the substrate comprising the first metal oxide and the second metal oxide and converting at least some of the additional first metal compound to form additional first metal oxide.

Still other embodiments of the present invention relate to applying additional second metal compound to the additional first metal oxide; and converting at least some of the additional second metal compound to form additional second metal oxide.

In some embodiments metal oxides suitable for metal oxide electrolytes comprise zirconium oxides combined with various transition and/or rare earth metals, including, but not limited to, scandium, yttrium, erbium, ytterbium, europium, gadolinium, or dysprosium, or combinations thereof. In one embodiment, a metal oxide suitable for one or more layers of an electrolyte comprises zirconium oxide ($ZrO_2$) or yttria-stabilized zirconia (YSZ) $Zr_{(1-x)}Y_xO_{[2-(x/2)]}$, x=0.08-0.20 or 0.10-0.50, or 0.15-0.20, in certain embodiments. In another embodiment, a suitable electrolyte metal oxide comprises scandia-stabilized zirconia (SSZ) $Zr_{(1-x)}Sc_xO_{[2-(x/2)]}$, x=0.09-0.11. Additional suitable electrolyte zirconium compounds comprise zirconium silicate ($ZrSiO_4$), $Zr_{0.85}Ca_{0.15}O_{1.85}$ or $3ZrO_2 2CeO_2+10\% CaO$.

In another embodiment metal oxides of an electrolyte comprise cerium oxides of the general formula $Ce_{(1-x)}M_xO_{(2-\delta)}$, x=0.10-0.20, and $\delta=x/2$. In some embodiments M samarium or gadolinium to produce $CeO_2$—$Sm_2O_3$ or $CeO_2$—$Gd_2O_3$.

Additional metal oxides suitable for electrolytes of solid oxide cells of the present invention, comprise perovskite structured metal oxides. In some embodiments, perovskite structured metal oxides comprise lanthanum gallates ($LaGaO_3$). Lanthanum gallates, in some embodiments, are doped with alkaline each metals or transition metals, or combinations thereof. In another embodiment, a perovskite structure metal oxide comprises lanthanum strontium gallium magnesium oxide (LSGM) $La_{(1-x)}Sr_xGa_{(1-y)}Mg_yO_{(3-\delta)}$, x=0.10-0.20, y=0.15-0.20, and $\delta=(x+y)/2$.

In a further embodiment, metal oxides suitable for electrolytes comprise brownmillerites, such as barium indiate ($Ba_2In_2O_6$), non-cubic oxides such as lanthanum silicate, neodymium silicate, or bismuth based oxide, or combinations thereof.

Electrolytes of solid oxide cells, according to some embodiments of the present invention, comprise a plurality of nanocrystalline grains, the nanocrystalline grains comprising one or more of the metal oxides that are suitable for use as an electrolyte in a solid oxide cell. In some embodiments, the nanocrystalline grains have an average size of less than about 50 nm. In other embodiments, nanocrystalline grains of electrolyte layers have an average size ranging from about 2 nm to about 40 nm or from about 3 nm to about 30 nm in another embodiment, nanocrystalline grains have an average size ranging from about 10 nm to about 25 nm. In a further embodiment nanocrystalline grains have an average size less than about 10 nm or less than about 5 nm.

Electrolytes of solid oxide cells are substantially non porous, in some embodiments in one embodiment, an electrolyte has a porosity less than about 20%. In another embodiment, an electrolyte has a porosity less than about 15% or less than about 10%. In a further embodiment, an electrolyte has a porosity less than about 5% or less than about 1%. In one embodiment, an electrolyte is fully dense meaning that the electrolyte has no porosity.

Once the metal oxide is formed, in some embodiments of the present invention, one or more epoxies can be applied to the metal oxide. In addition, or alternatively, epoxy can be applied to other components, such as one or more electrodes of the solid oxide cell. Epoxy can be used, in some embodiments of the present invention, to seal the solid oxide cell so that reactants from one side of the cell do not penetrate to the other side of the cell. Any suitable epoxy that can withstand the operating temperature of the solid oxide cell can be used alone or in combination. U.S. Pat. No. 4,925,886 to Atkins et al, discloses and claims epoxy compositions composing two epoxies and having a usable temperature of at least 160° C., for example, U.S. Pat. No. 6,624,213 to George et al. reports tests of various epoxy compositions at 177° C., for further examples. The '886 patent and the '213 patent are incorporated by reference herein in their entireties.

In some embodiments an electrolyte has a thickness (distance between a cathode and an anode) ranging from about 1 nm to about 1 mm or from about 10 nm to about 500 µm. In other embodiments, an electrolyte has a thickness ranging from about 50 nm to about 250 µm, from about 100 nm to about 100 µm, or from about 500 nm to about 50 µm. In another embodiment, an electrolyte has a thickness ranging from about 750 nm to about 10 µm, or from about 1 µm to about 5 µm, or from about 1.2 µm to about 4 µm, or from about 1.5 µm to about 2 µm. In a further embodiment, an electrolyte has a thickness less than about 10 µm or less than about 1 µm. In one embodiment, an electrolyte has a thickness ranging from about 1 nm to about 100 nm or from about 50 nm to about 100 nm. In still other embodiments, an electrolyte has a thickness greater than about 500 µm.

Materials suitable for use in air electrodes, fuel electrodes, electrolyzer electrodes, sensors, and/or electrolytes, in addition to the materials recited hereinabove, can be chosen from $CeO_2$—$ZrO_2$ wherein $CeO_2$ about 10-90 weight percent; yttria-stabilized zirconia (YSZ) wherein yttria is present in an amount of about 1-50 mol percent; $CeO_2$—$PrO_2$ wherein $PrO_2$ is up to about 50 weight percent; $PrO_2$—$CeO_2$—$ZrO_2$ wherein $PrO_2$—$CeO_2$ is up to about 90 weight percent. $PrO_2$—$ZrO_2$ wherein $PrO_2$ is 10 to 90 weight percent; scandia-doped zirconia (SSZ) doped with one or more of $Co_3O_4$, $Bi_2O_3$, $SiO_2$, $TiO_2$, $Fe_2O_3$, NiO, $MnO_2$, $CeO_2$, and $Al_2O_3$; YSZ doped with one or more of $Co_3O_4$, $Bi_2O_3$, $SiO_2$, $TiO_2$, $Fe_2O_3$, NiO, $MnO_2$, $CeO_2$, and $Al_2O_3$; CaO stabilized zirconia doped with one or more of $Co_3O_4$, $Bi_2O_3$, $SiO_2$, $TiO_2$, $Fe_2O_3$, NiO, $MnO_2$, $CeO_2$, and $Al_2O_3$, mixed LSM and YSZ; and combinations thereof. The relative amounts of the various oxides are not limited. In some embodiments for example YSZ comprises about 8 mole percent $Al_2O_3$. In other embodiments, about 30 mole percent $Al_2O_3$ is present in still further embodiments about 90 mole percent $Al_2O_3$ appears. In yet another embodiment, a metal oxide comprises cerium, samarium, and oxygen in the approximate mole ratios 0.85:0.15:1.925. An additional embodiment provides cerium, gadolinium, and oxygen in the approximate mole ratios or 0.9:0.1:1.95.

Oxides of the following elements can be used in embodiments of air electrodes, fuel electrodes, electrolyzer electrodes, sensors, and/or electrolytes in some embodiments of the present invention: lithium, beryllium, sodium, magnesium, aluminum, silicon, potassium, calcium, scandium, titanium, vanadium, chromium, manganese, iron, cobalt, nickel, copper, zinc, gallium, germanium, arsenic, bromine, rubidium, strontium, yttrium, zirconium, niobium, molybdenum, technetium, ruthenium, rhodium, palladium, antimony, tellurium, silver, cadmium, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten rhenium, osmium, iridium, gold, mercury, thallium, lead, bismuth, radium, actinium, platinum, thorium, protactinium, uranium, neptunium, plutonium, americium, berkelium, californium, einsteinium, fermium, mendelevium, nobelium, lawrencium, or curium. Oxides containing more than one of the foregoing elements, and oxides containing elements in addition to the foregoing elements, also can be used in embodiments of the present invention. For example, alumina containing small amounts of chromium, titanium, iron, vanadium, and combinations thereof, akin to the mineral corundum and gemstones sapphire and ruby, can be used in certain embodiments.

Moreover, in some embodiments, one or more catalytic materials can be incorporated into each of the foregoing metal oxide materials in an amount ranging from about 0.5 to about 10 weight percent. In other embodiments, one or more catalytic materials can be incorporated in an amount less than about 5 weight percent. In still other embodiments, one or more catalytic materials can be incorporated in an amount greater than about 10 weight percent.

In some embodiments of solid oxide cells of the present invention, an electrode-electrolyte transition layer is interposed between the electrolyte and the electrode. An electrode-electrolyte transition layer comprises both electrode a no electrolyte materials. By composing both electrode and electrolyte materials the electrode-electrolyte transition layer, in some embodiments is operable to reduce disparities in coefficients of thermal expansion between the electrode and electrolyte. Reducing such disparities can have an inhibitory effect on degradative pathways such as cracking or delamination between the electrode and electrolyte. Moreover, an electrode-electrolyte transition layer provides increased stability by anchoring the electrolyte to the electrode. The electrode-electrolyte transition layer, in some embodiments additionally provides a robust base on which to further build an electrolyte, the electrolyte having thickness less than about 10 µm or less than about 1 µm, in some cases.

In some embodiments, an electrode-electrolyte transition layer has a thickness ranging from about 1 nm to about 5 nm, from about 5 nm to about 10 nm from about 10 nm to about 20 nm, from about 20 nm to about 50 nm, from about 50 nm to about 100 nm or from about 20 nm to about 80 nm. In another embodiment an electrode-electrolyte transition layer has a thickness ranging from about 30 nm to about 60 nm or from about 40 nm to about 50 nm. In a further embodiment, an electrode-electrolyte transition layer has a thickness less than about 10 nm or greater than about 100 nm.

FIG. 1 is a micrograph at approximately two million× magnification illustrating an electrode-electrolyte transition layer according to one embodiment of the present invention. In the micrograph, a YSZ electrolyte (102) is disposed on an electrode substrate (104) made of stainless steel 304. An electrode-electrolyte interlayer (106) is interposed between the YSZ electrolyte (102) and the electrode substrate (104).

Electrodes

Electrodes of the present invention, in some embodiments, comprise a substrate. In some embodiments, a substrate comprises silicon carbide doped with titanium. In other embodiments, a substrate comprises $La_{1-x}Sr_xMnO_3$ [lanthanum strontium doped manganite (LSM)]. In another embodiment, a substrate comprises one or more porous steel alloys. In one embodiment, a porous steel alloy composes steel alloy 52. In some embodiments, a porous steel alloy suitable for use as an electrode substrate comprises steel alloy 316, stainless steel alloy 430, Crofer 22 APU® (Thyssen Krupp), E-Brite® (Alleghany Ludium). HASTELLOY® C-276, INCONEL® 600, or HASTELLOY® X, each of which is commercially available from Mott Corporation of Farmington, Conn. Yet additional embodiments provide an electrode substrate comprising nickel such as, for example, Nickel Alloy 200. Certain embodiments employ an electrode comprising porous graphite, optionally with one or more catalytic materials in a further embodiment a substrate comprises any metal or alloy known to one of skill in the art operable to serve as an electrode. Some embodiments of the present invention provide electrode substrates comprising a metal, a metal carbide, or a combination thereof. Certain additional embodiments provide an electrode substrate comprising titanium silicate carbide. In some of those embodiments, the electrode substrate material may have electrical, structural, and mechanical properties that are better than those of ceramic electrodes.

Electrode substrates, according to further embodiments of the present invention, are porous. In some embodiments, a substrate has a porosity ranging from about 5% to about 40%. In another embodiment, a substrate has a porosity ranging from about 10% to about 30% or from about 15% to about 25%. In a further embodiment, a substrate has a porosity greater than about 40%. A substrate, in some embodiments, has a porosity ranging from about 40% to about 80%. In one embodiment a substrate has a porosity greater than about 80%.

In addition to a substrate, some electrodes of the present invention optionally compose a coating disposed on the substrate, the coating comprising at least one layer of at least one metal oxide. In some embodiments, a coating disposed on the substrate comprises a plurality of layers comprising one or more metal oxides. Metal oxide layers suitable for use in electrodes of the present invention can comprise any of the metal oxides recited herein, including cerium samarium oxides. Some embodiments of the present invention provide a metal oxide coating disposed on the electrode substrate that can act as an electrolyte, an electrode-electrolyte transition layer, a concentration-gradient layer, a matching layer for coefficients of thermal expansion, an electrical insulator, or a combination thereof, among other functions.

Substrate coatings composing one or more metal oxide layers, according to some embodiments of the present invention, are porous in one embodiment, a coating has a porosity ranging from about 5% to about 40% in another embodiment, a coating has a porosity ranging from about 10% to about 30% or from about 15% to about 25%. In a further embodiment, a substrate coating has a porosity greater than about 40%. A substrate coating, in some embodiments, has a porosity ranging from about 40% to about 60%. In one embodiment a substrate coating has a porosity greater than about 60%.

Substrate coatings can have any desired thickness, in one embodiment a substrate coating has a thickness ranging from about 1 nm to about 1 micron. In another embodiment, a substrate coating has a thickness ranging from about 50 nm to about 750 μm from about 500 nm to about 500 μm, from about 1 μm to about 350 μm, or from about 10 μm to about 200 μm, in a further embodiment, a substrate coating has a thickness ranging from about 50 μm to about 100 μm. In some embodiments wherein a coating comprises a plurality of metal oxide layers each metal oxide layer has a thickness ranging horn about 5 nm to about 15 nm, wherein the total thickness of the coating is the summation of the thicknesses of the individual layers.

In some embodiments of electrodes of the present invention, a substrate-coating transition layer is interposed between the substrate and the coating. A substrate-coating transition layer composes both substrate and coating materials. By comprising both substrate and coating materials, the substrate-coating transition layer, in some embodiments, is operable to reduce disparities in coefficients of thermal expansion between the substrate and the metal oxide coating of the electrode. Reducing such disparities can have an inhibitory effect on degradative pathways such as cracking or delamination between the substrate and metal oxide coating. Moreover, a substrate-coating transition layer provides increased stability by anchoring the metal oxide coating to the electrode.

In some embodiments, a substrate-coating transition layer has a thickness ranging from about 3 nm to about 100 nm or from about 20 nm to about 80 nm. In another embodiment, a substrate-coating transition layer has a thickness ranging from about 30 nm to about 50 nm or from about 40 nm to about 50 nm. In a further embodiment, a substrate-coating transition layer has a thickness less than about 10 nm or greater than about 100 nm.

Electrodes, according to some embodiments of the present invention further comprise catalytic materials. Catalytic materials can comprise transition metals including, but not limited to, platinum, palladium, rhodium, nickel, cerium, gold, silver, zinc, lead, ruthenium, rhenium, or mixtures thereof. Catalytic materials, in some embodiments, are disposed in one or a plurality of metal oxide layers coating the substrate of an electrode. The combination of a metal oxide with pure metals or alloys, in some embodiments, produces a cermet. Electrodes of solid oxide fuel cells further comprising catalytic materials can function as fuel reformers operable to convert hydrocarbon fuels into hydrogen for subsequent use in the solid oxide fuel cell, in some embodiments. Moreover, electrodes further comprising catalytic materials can function as fuel reformers upstream and independent from the solid oxide fuel cell in other embodiments.

Electrodes comprising catalytic materials can additionally demonstrate compositional gradients based on the distribution of the catalytic materials in the plurality of metal oxide layers. In one embodiment, an electrode comprises a substrate and a plurality of metal oxide layers disposed on the substrate, wherein metal oxide layers closer to the substrate comprise greater amounts of catalytic material than metal oxide layers further from the substrate. Moreover, in another embodiment, metal oxide layers further from the substrate comprise greater amounts of catalytic material than metal oxide layers closer to the substrate. In one embodiment, for example, metal oxide layers further from the substrate comprise about 5 weight percent catalytic material while metal oxide layers closer to the substrate compose about 1 weight percent catalytic material.

Electrodes of the present invention, in some embodiments, are resistant to harsh environments and venous chemical species which can foul the electrodes, such as sulfur or carbon. An electrode, in one embodiment, is an anode. An electrode, in another embodiment is a cathode. In some embodiments the metal oxide coating of an electrode can protect the electrode substrate from corrosion and/or degradation.

Turning now to components that can be included in solid oxide fuel cells, solid oxide fuel cells of the present invention comprise an air electrode. The air electrode of a solid oxide fuel cell operates as a cathode to reduce oxygen molecules thereby producing oxygen anions for subsequent transport through the electrolyte. In some embodiments, an air electrode composes p-type semiconducting oxides such as lanthanum manganite ($LaMnO_3$). Lanthanum manganite can be doped with rare earth elements, such as strontium, cerium, and/or praseodymium to enhance conductivity. In one embodiment, an air electrode comprises $La_{1-x}Sr_xMnO_3$ [lanthanum strontium doped manganite (LSM)]. In another embodiment, an air electrode comprises lanthanum strontium ferrite or lanthanum strontium cobaltite or a combination thereof.

Air electrodes, according to some embodiments of the present invention, are porous. In one embodiment an air electrode has a porosity ranging from about 5% to about 30%. In another embodiment, an air electrode has a porosity ranging from about 10% to about 25% or from about 15% to about 20%. In a further embodiment, an air electrode has a porosity greater than about 30%. An air electrode, in some embodiments, has a porosity ranging from about 30% to about 60% or from about 40% to about 80%. In one embodiment, an air electrode has a porosity greater than about 80%.

In addition to an air electrode, a solid oxide fuel cell comprises a fuel electrode. A fuel electrode, in some embodiments, comprises one or more metal oxides combined with one or a plurality of catalytic materials. Catalytic materials, as provided herein, comprise transition metals including, but not limited to, platinum, palladium, rhodium, nickel, cerium gold, silver, zinc, lead, ruthenium, rhenium, or mixtures thereof. In one embodiment, a fuel electrode comprises zirconia ($ZrO_2$) combined with Ni. Yttria-stabilized zirconia (YSZ), $Zr_{(1-x)}Y_xO_{[2-(x/2)]}$, for example, can be combined with Ni to produce a Ni—YSZ fuel electrode. Catalytic materials, in some embodiments, are incorporated into metal oxide compositions of fuel electrodes in an amount ranging from about 0 to about 10 weight percent. In other embodiments, catalytic materials are incorporated into metal oxide compositions of fuel electrodes in an amount leas than about 5 weight percent, less than about 0.5 weight percent, or greater than about 10 weight percent.

Fuel electrodes, according to some embodiments of the present invention, are porous. In one embodiment, a fuel electrode has a porosity ranging from about 5% to about 40%. In another embodiment, a fuel electrode has a porosity ranging from about 10% to about 30% or from about 15% to about 25%. In a further embodiment, a fuel electrode has a porosity greater than about 40%. A fuel electrode, in some embodiments, has a porosity ranging from about 40% to about 80%. In still other embodiments, a fuel electrode has a porosity greater than about 80%.

In order to reduce problems and disadvantages associated with variances in coefficients of thermal expansion between electrode and electrolytes of solid oxide cells, electrodes, in some embodiments of the present invention, compose compositional gradients. An electrode, in one embodiment, comprises a region closer to the electrolyte and a region further from the electrolyte, wherein the region closer to the electrolyte comprises a greater amount of electrolyte material than the region of the electrode further mom the electrolyte. In another embodiment, an electrode of a solid oxide cell composes a plurality of layers. Layers of the electrode closer to the electrolyte comprise greater amounts of electrolyte material than layers of the electrode further from the electrolyte. A solid oxide cell, in some embodiments, comprises a first electrode comprising a plurality of layers of a first material and an electrolyte comprising an electrolyte material disposed on the first electrode, wherein layers of the first material closer to or adjacent to the electrolyte further comprise greater amounts of the electrolyte material than layers of the first material further from or spaced apart from the electrolyte.

In addition to variances in coefficients of thermal expansion, some of the solid oxide cells of the present invention also address fuel, air and other reactant delivery mechanisms by providing electrodes comprising porosity and optionally, porosity gradients. For example, electrodes of solid oxide fuel cells may be porous in order to allow the ingress of air and fuel to the electrolyte and the egress of other gases produced or not consumed by the fuel cell. In one embodiment a solid oxide cell comprises a solid electrolyte disposed on a first electrode, the first electrode comprising a first region closer to the solid electrolyte and a second region further from the electrolyte, wherein the first region has a porosity less than the second region. Alternatively, in another embodiment, the first region of the electrode has a porosity that is greater than the second region of the electrode.

Moreover, in some embodiments, a solid oxide cell comprises a first electrode comprising a plurality of layers of a first material and a solid electrolyte disposed on the first electrode, wherein layers of the first material closer to the solid electrolyte have porosities less than layers of the first material further from the solid electrolyte. Alternatively, in other embodiments, layers of the first material closer to the solid electrolyte have porosities greater than layers of the first material further from the solid electrolyte.

Interconnects

In another aspect, the present invention provides interconnects operable to be used in solid oxide cells as well as other applications. Interconnects of the present invention, in some embodiments, are resistant to harsh environments and chemical species which can degrade the interconnects. In one embodiment, the present invention provides an interconnect comprising a substrate comprising a first material, a coating composition comprising a layer of a metal oxide disposed on the substrate, and optionally a substrate-coating transition layer interposed between the substrate and the coating. In some embodiments, a coating composition composes a plurality or metal oxide layers. One or a plurality of metal oxide coatings can assist in protecting a metallic or ceramic interconnect substrate from degradative conditions and/or chemical species.

Interconnects, in some embodiments, comprise substrates. In certain embodiments, substrates compose metal oxides including, but not limited to, lanthanum and yttrium chromites. In other embodiments, a substrate comprises metals or alloys, such as chromium based alloys. In one embodiment a chromium based alloy comprises 5 weight percent iron and 1 weight percent yttria. In another embodiment, a substrate comprises a ferritic steel. In a further embodiment, a substrate composes any metal operable to sufficiently transfer charge carriers into or from an external circuit. Thus, in some embodiments, interconnects of the present invention are adaptable to provide electrical communication between a electrode and an external circuit. In further embodiments, interconnects are adaptable to provide material communication between an electrode and an external source of a material, and/or an exit for a material. For example, an interconnect can provide air or oxygen to the cathode of a solid oxide fuel cell. For another example, an interconnect can provide an exhaust conduit for water or steam to exit a solid oxide fuel cell. For yet another example, an interconnect can provide a conduit to a storage system for hydrogen generated at the cathode of a solid oxide electrolyzer cell. In still other embodiments, an interconnect provides both electrical and material communication between a electrode and an external circuit and external sources and/or reservoirs and/or exhaust for material. Optionally, an interconnect may be adapted to provide thermal communication between an electrode and an external source or sink for thermal energy.

Accordingly interconnects can have any desired shape. Wires, films, monoliths, porous monoliths, disks, tubes pipes, among other shapes, are possible. Connections between an interconnect and an electrode can adopt any suitable form. In some embodiments, the same piece of metal (or metal carbide, cermet, or other material) forms the substrate for the electrode and for the interconnect; in such embodiments, the portion of the metal that engages in the electrochemical reaction in the call is the electrode portion, while the portion of the metal providing communication outside the cell is the interconnect portion. In other embodiments electrical contact between the interconnect and the electrode are made with any suitable connection, such as, for example, welding, stamping, melt fusion, mechanical connections such as bolts or rivets, conductive paints such as silver paint, sputtered metals, and conductive adhesives, as well as combinations thereof. Such connections can be made before, during, or after formation of metal oxides as described herein.

Interconnect substrates can have any desired thickness. In one embodiment a substrate has a thickness ranging from about 1 nm to about 1 mm. In another embodiment, a substrate has a thickness ranging from about 50 nm to about 750 μm, from about 500 nm to about 500 μm, from about 1 μm to about 350 μm, or from about 10 μm to about 200 μm. In a further embodiment, a substrate has a thickness ranging from about 50 μm to about 100 μm.

In addition to a substrate, an interconnect of some embodiments of the present invention comprises a coating disposed on the substrate, the coating comprising a layer of a metal oxide. In some embodiments, a coating disposed on the substrate composes a plurality of layers comprising one or more metal oxides. Metal oxide layers suitable for use in interconnects of the present invention can compose any of the metal oxides recited herein, such as, for example, any of the cerium samarium oxides.

Substrate coatings comprising one or more metal oxide layers, according to some embodiments of the present invention, are porous. In one embodiment, a coating has a porosity ranging from about 5% to about 40%. In another embodiment, a coating has a porosity ranging from about 10% to about 30% or from about 15% to about 25%. In a further embodiment, a substrate coating has a porosity greater than about 40%. A substrate coating, in some embodiments, has a porosity ranging from about 40% to about 60%. In one embodiment, a substrate coating has a porosity greater than about 60%.

Substrate coatings can have any desired thickness. In one embodiment, a substrate coating has a thickness ranging from about 1 nm to about 1 micron. In another embodiment, a substrate coating has a thickness ranging from about 50 nm to about 750 µm, from about 500 nm to about 500 µm, from about 1 µm to about 350 µm, or from about 10 µm to about 200 µm. In a further embodiment, a substrate coating has a thickness ranging from about 50 µm to about 100 µm. In some embodiments wherein a coating comprises a plurality of metal oxide layers, each metal oxide layer has a thickness ranging from about 5 nm to about 15 nm, wherein the total thickness of the coating is the summation of the thicknesses of the individual layers.

In some embodiments of interconnects of the present invention, a substrate-coating transition layer is interposed between the substrate and the coating. A substrate-coating transition layer comprises both substrate and coating materials. By comprising both substrate and coating materials, the substrate-coating transition layer, in some embodiments, is operable to reduce disparities in coefficients of thermal expansion between the substrate and the metal oxide coating of the interconnect. Reducing such disparities can have an inhibitory effect on degradative pathways such as cracking or delamination between the substrate and metal oxide coating. Moreover, a substrate-coating transition layer provides increased stability by anchoring the metal oxide coating to the electrode.

In some embodiments a substrate-coating transition layer of an interconnect has a thickness ranging from about 3 nm to about 100 nm or from about 20 nm to about 80 nm. In another embodiment, a substrate-coating transition layer has a thickness ranging from about 30 nm to about 60 nm or from about 40 nm to about 50 nm. In a further embodiment a substrate-coating transition layer has a thickness less than about 10 nm or greater than about 100 nm.

Additionally, in order to reduce problems and disadvantages associated with variances in coefficients of thermal expansion between interconnects and electrodes of solid oxide cells, interconnects, in some embodiments of the present invention, comprise compositional gradients. An interconnect, in one embodiment, composes a region closer to a cathode and a region further from the cathode, wherein the region closer to the cathode has a greater amount of cathode material than the region of the interconnect further from the cathode. Moreover, in another embodiment, an interconnect comprises a region closer to an anode and a region further from the anode, wherein the region closer to the anode has a greater amount of anode material than the reason of the interconnect further from the anode.

In another embodiment, an interconnect comprises a substrate coated with a plurality of metal oxide layers. Layers of the interconnect closer to the cathode comprise greater amounts of cathode material than layers of the interconnect further from the cathode. Moreover, in another embodiment, layers of the interconnect closer to the anode comprise greater amounts of anode material than layers of the interconnect further from the anode.

Electrolyzers

Some embodiments of the present invention provide solid oxide electrolyzer cells or a component thereof comprising a metal oxide. In certain embodiments the electrolyzer cell or component thereof is substantially identical in manufacture and composition as the other solid oxide cells and components described herein.

In some of those embodiments of the present invention where the same cell can function as an electrolyzer cell and alternately as a fuel cell simply by reversing the flow of electrons, the cathode of the electrolyzer corresponds to the fuel electrode of the fuel cell; and the anode of the electrolyzer corresponds to the air electrode of the fuel cell. Those of ordinary skill in the art recognize that oxidation occurs at the anode and reduction occurs at the cathode, so the name of a given electrode may differ depending on whether the cell operating as an electrolyzer or as a fuel cell.

In other embodiments, electrons flow in the same direction, regardless of whether the cell is electrolyzing or producing electricity. This can be accomplished, for example, by supplying oxygen anions to a given electrode in electrolysis mode, and alternately supplying hydrogen to the same electrode in fuel cell mode. Such an electrode will function as the oxidizing anode in either mode.

Accordingly, some embodiments of the present invention provide a solid oxide electrolyzer cell, comprising a first electrode, a second electrode, and a metal oxide electrolyte interposed between the first electrode and the second electrode.

The present invention also provides, in some embodiments, a method for making a product, comprising:
providing a solid oxide cell comprising a first electrode, a second electrode,
and a metal oxide electrolyte interposed between the first electrode and the second electrode, wherein the metal oxide electrolyte has an ionic conductivity greater than the bulk ionic conductivity of the metal oxide;
contacting the first electrode with a reactant; and
supplying electrical energy to the first electrode and the second electrode thereby causing the reactant to undergo electrochemical reaction to yield the product.

The skilled electrochemist will appreciate that a complete circuit is necessary for electrical energy to cause electrochemical reaction. For example, at least one ion may traverse the metal oxide electrolyte to complete the electrical circuit at the second electrode. Moreover, a second product may be formed at the second electrode due to electrochemical reaction. Therefore, some embodiments further provide for contacting the second electrode with a second reactant, thereby causing the second reactant to undergo electrochemical reaction to yield a second product. Contacting an electrode and supplying electrical energy can occur in any suitable order in a continuous process, electrical energy supply is maintained while additional reactant(s) enter the cell and product(s) are removed.

Any suitable reactant can be supplied to an electrode for electrochemical reaction. Suitable reactants include, but are not limited to, water such as, for example, pure water, fresh water, rain water, ground water, salt water, purified water, deionized water, water containing a ionic substance, brine, acidified water, basified water, hot water, superheated water, steam, carbon dioxide, carbon monoxide, hydrogen, nitrous oxides, sulfur oxides, ammonia, metal salts, molten metal salts, and combinations thereof. Ionic substances include those substances that release a ion when placed in contact with water, and include, but are not limited to, salts, acids, bases, and buffers. Reactants, and for that matter, products, can be in any suitable form, including solid, liquid, gas, and combinations thereof. Solid reactants and/or solid products lend themselves to batch processes, although suitable methods for continuously removing a solid product from a cell can be employed. Fluid reactants and products can appear in either batch or continuous processes. Optionally, heat energy is applied to the reactant, the product, at least one electrode, the metal oxide, the cell, or a combination thereof.

Some embodiments provide a sacrificial electrode. A sacrificial electrode itself reacts in the electrolysis process, and is thereby consumed or rendered unreactive as the reaction proceeds. For example, a zinc electrode can be consumed in a suitable solid oxide cell reaction, yielding $Zn^{2+}$ and two electrons per atom of zinc consumed. In another example, an electrode can become coated and thereby rendered unreactive by solid product forming on its surface. The unreactive electrode can be removed from the cell, and the product extracted from the electrode, or the product can be used on the electrode in another process. The electrode then can be regenerated, recycled, or discarded. Alternatively, a sacrificial electrode can be made to gradually insert into a cell at a rate consistent with the rate at which the electrode is consumed.

A reactant undergoing electrochemical reaction can be oxidized and/or reduced, and chemical bonds may form and/or break. For example, when water undergoes electrolysis, hydrogen-oxygen bonds break, $H^+$ is reduced to $H^0$, $O^{2-}$ is oxidized to $O^0$, and $H_2$ and $O_2$ form, in some circumstances. Hydrogen peroxide and other species may form in other circumstances. The skilled artisan will appreciate that many electrode half reactions can be substituted so that any variety of anions, cations, and other species may result from electrochemical reaction.

In one embodiment, water containing NaCl can be electrolyzed to form hydrogen gas and NaOH at the cathode and chlorine gas at the anode, in the so-called chlor-alkali process:

$$2NaCl(aq) + 2H_2O(l) \rightarrow 2NaOH(aq) + Cl_2(g) + H_2(g)$$

A solid oxide cell arranged to carry out that reaction, in some embodiments, provides water containing a high concentration of NaCl (for example, saturated) to a first electrode that will act as an anode, and provides water to a second electrode that will act as a cathode. The cell also provides liquid effluent collection to remove the depleted NaCl solution from the anode, and NaOH-containing water from the cathode. The cell further provides gas effluent collection to remove chlorine gas from the anode and hydrogen gas from the cathode. Optionally, the hydrogen and chlorine can be subject to electrochemical reaction to release the electrochemical energy stored by the foregoing electrolysis, or they can be used for other industrial processes, such as the synthesis of sodium hypochlorite.

The present invention also provides methods for storing electrochemical energy. In some embodiments, a reactant is supplied to an electrode of a solid oxide cell, the reactant undergoes one or more electrochemical reactions and yields a fuel, thereby storing electrochemical energy. The electrochemical reaction may also yield other products, such as cations, anions, and other species, some of which may form at a second electrode of the solid oxide cell that completes an electrical circuit. A first electrode and a second electrode are separated by a metal oxide electrolyte in the solid oxide cell. The fuel can be subjected to energy conversion processes such as reverse electrochemical reaction in a fuel cell or battery, combustion, and the like to release the stored electrochemical energy.

In one embodiment, electrochemical energy is stored by providing a reactant to a cathode; reducing the reactant at the cathode to release an anion and a fuel; storing the fuel, transporting the anion through a metal oxide electrolyte to anode; and oxidizing the anion. Optionally, the oxidized anion is stored as well, separately from the stored fuel. Thus in one embodiment, water in a suitable form is supplied to a cathode, at which it is reduced to hydrogen ($H_2$) and oxygen anion ($O^{2-}$); the hydrogen is collected and stored, while the oxygen anion diffuses through a solid metal oxide electrolyte to an anode where the oxygen anion is oxidized to oxygen ($O_2$). Optionally, in the foregoing non-limiting example, the oxygen is collected and stored as well.

When desired, the stored hydrogen can be fed to any suitable fuel cell, including but not limited to the cell that produced the hydrogen, and the hydrogen can be oxidized to release the stored electrochemical energy. Any suitable gas can be fed to the air electrode of the fuel cell, such as, for example, the optionally-stored oxygen, other oxygen, other oxygen-containing gas such as air, and combinations thereof. Alternatively, the stored hydrogen can be combusted with oxygen to propel a rocket, drive a piston, rotate a turbine, and the like. In other embodiments, the stored hydrogen can be used in other industrial processes, such as petroleum cracking.

Some embodiments involve those reactants that yield the high energy materials commonly found in primary (nonrechargeable) and secondary (rechargeable) batteries. For secondary battery materials, the low-energy (discharge) state materials may be produced, since secondary batteries can be charged before first use. Such materials include, but are not limited to, $MnO_2$, $MnSO_3$, $NH_4Cl$, $HNO_3$, $LiCl$, $Li$, $Zn$, $ZnO$, $ZnCl_2$, $ZnSO_4$, $HgO$, $Hg$, $NiOOH$, $Ni(OH)_2$, $Cd$, $Cd(OH)_2$, $Cu$, $CuSO_4$, $Pb$, $PbO_2$, $H_2SO_4$, and $PbSO_4$.

At least some embodiments of fuel cells described above can be used to provide electrolyzer cell embodiments of the present invention. While fuel cell embodiments optionally employ one or more of fuel supply, air or oxidizer supply, interconnects, and electrical energy harvesting means (e.g., wires forming a circuit between the fuel and air electrodes' interconnects), electrolyzer cell embodiments optionally employ one or more of reactant supply, fuel collection, interconnects, and electrical energy supply. Optionally, electrolyzer cell embodiments also provide collection means for other products in addition to fuel. The reactant supply provides any suitable reactant for electrolysis. Fuel collection, in some embodiments, involves collecting hydrogen for storage and later use. Storage vessels, metal hydride technology, and other means for storing hydrogen are known in the art. Fuel collection, in other embodiments, involves collection of, for example, carbon-coated electrodes for later oxidation. Alternatively, carbon can be formed into fluid hydrocarbon for easy storage and later combustion or reformation. Hydrocarbon formation requires a supply of hydrogen molecules, atoms, or ions in a suitable form to combine with carbon at the cathode, in some embodiments Other product collection involves, in some embodiments, the collection of oxygen for storage and safer use.

In still other embodiments, an electrolyzer cell is capable of performing other electrolysis tasks, such as electroplating. In such embodiments, a metal oxide functions as a solid electrolyte shuttling a ion to complete an electrical circuit.

In some embodiments, the electrodes of the electrolyzer cell are adapted for the particular electrochemistry expected to occur at the given electrode. For example, the electrode can comprise one or more catalytic materials to facilitate the electrochemical reaction.

Sensors

Some embodiments of the present invention provide solid oxide sensors or components thereof. Like the fuel cells and electrolyzer cells described herein sensors or the present invention compose a metal oxide electrolyte. In some embodiments, at least one ion passes through that metal oxide electrolyte during cell operation. In other embodiments, the solid oxide cells useful as sensors or components thereof are substantially identical to the solid oxide cells and components described above. The metal oxide electrolyte of sensors in certain embodiments has been made according to a process comprising:

applying a metal compound to a substrate, and
converting at least some of the metal compound to a metal oxide,
wherein the metal oxide electrolyte has an ionic conductivity greater than the bulk some conductivity of the metal oxide. The metal oxide electrolyte obtains a greater ionic conductivity for example by including another material such as a nanobar or a thin sheet as described herein.

Sensors according to various embodiments of the present invention can be used to detect any suitable analyte or analytes. Oxygen sensors, useful as lambda sensors in automotive exhaust systems, or as oxygen partial pressure detectors in rebreather systems, represent some applications for embodiments. Other sensors, such as gas sensors including but not limited to CO, $CO_2$, $H_2$, $NO_x$, and $SO_x^-$, ion sensors including but not limited to pH meters, $K^+$, and $Na^+$; biosensors including but not limited to glucose sensors and other enzyme electrodes, electrochemical breathalyzers; and electronic noses; represent other applications for embodiments of the present invention. Many such sensors function at least in part due to the diffusion of an ion through an electrolyte which electrolyte comprises a metal oxide.

Accordingly, additional embodiments provide a method for detecting an analyte, comprising:

providing a sensor for the analyte, wherein the a sensor comprises a metal oxide made by a process composing:
  applying a metal compound to a substrate, and
  converting at least some of the metal compound to the metal oxide,
    wherein the metal oxide electrolyte has an ionic conductivity
    greater than the bulk ionic conductivity of the metal oxide; and
passing an ion through the metal oxide to detect the analyte. The metal oxide electrolyte obtains a greater ionic conductivity for example by including another material such as a nanobar or a thin sheet as described herein. Passing an ion through a metal oxide can include any suitable transport mechanism, such as, for example diffusion. In addition, movement along metal oxide crystal grain boundaries represents another transport mechanism, in some embodiments. Detecting an analyte can indicate obtaining any useful information about the analyte such as for example, determining its mere presence, concentration, partial pressure, oxidation state, or combinations thereof. And, sensors of the present invention can be designed for any suitable environment, such as solid, semisolid (e.g., soil), liquid gas, plasma, and combinations thereof. Also such sensors can be designed for any suitable operating temperature, ranging from the very cold to the very hot. Some solid oxide cells useful as sensors according to the present invention have an operating temperature of below about −195° C., below about −182° C., below about −77° C., from about −78° C. to about 0° C., from about 0° C. to about 100° C., from about 100° C. to about 400° C., from about 400° C. to about 600° C., from about 600° C. to about 900° C., from about 900° C. to about 1200° C., or above about 1200° C. Other embodiments useful as sensors have operating temperatures below about 0° C., above about 0° C., above about 100° C., or above about 500° C.

A few embodiments of the present invention provide solid oxide cells, useful as sensors, that enjoy one or more advantages over conventional sensors. In some embodiments, the metal oxide has a certain thickness, thinner than conventional sensors. In other embodiments, the solid oxide cell operates at a lower temperature, compared to conventional sensors. Still other embodiments provide smaller sensors. Even other embodiments provide sensors made from less-expensive materials. Additional embodiments have better-matched coefficients of thermal expansion between two or more materials in the cell. Still other embodiments provide one or more concentration gradients, one or more porosity gradients, or combinations thereof.

Further embodiments of the present invention provide a sensor composing at least two electrodes separated by a metal oxide that functions as a solid electrolyte. In some of those embodiments, the voltage difference between the at least two electrodes corresponds to the concentration of the analyte being detected at one of the electrodes. A first electrode functions as a reference electrode and is exposed to a reference environment. Suitable reference environments include but are not limited to, air, vacuum, standard solutions, and environments of known or controlled composition. In some embodiments, the reference environment is formed by arranging one or more materials that substantially isolate the reference electrode from the environment being measured. The second electrode is exposed to the environment being measured. Optionally, the second electrode comprises one or more catalytic materials in operation, the first and second electrodes are placed in electrical communication with one or more devices that can measure, for example, the voltage difference, the current, the resistance, or combinations thereof, between the two electrodes. Such devices are known in the art. Optionally, heat or cooling can be supplied to one or both electrodes, the electrolyte, or combinations thereof. Heat or cooling can come from any suitable source, such as, for example, one or more electrical resistance heaters, chemical reaction, thermal fluid in thermal communication with the sensor, the measured environment, and combinations thereof.

In some embodiments, a reference voltage is supplied to the electrodes, and the current needed to maintain the reference voltage corresponds to the concentration of the analyte being measured. For example, U.S. Pat. No. 7,235,171, describes two-electrode hydrogen sensors comprising barium-cerium oxide electrolyte. The '171 patent also indicates that various other metal oxides also function as electrolytes in hydrogen sensors, including selenium cerium oxides, selenium cerium yttrium oxides, and calcium zirconium oxides, which conduct protons, and oxygen anion conductors. The '171 patent is incorporated herein by reference in its entirety.

In other embodiments, a gas permeable porous platinum measuring electrode is exposed to a measured environment that contains a partial pressure of oxygen. A metal oxide, such as, for example, yttria-stabilized zirconia, separates the measuring electrode from a gas permeable porous platinum reference electrode that is exposed to air. The voltage difference, current, or both between the electrodes can be measured and correlated to the difference of partial pressure of oxygen between the measured environment and air. In some embodiments, the measured environment is an exhaust stream from the combustion of hydrocarbons.

In still other embodiments, at least two pairs of electrodes appear, wherein a metal oxide separates the electrodes in each pair. One of the two pairs functions as a reference cell while the other of the two pairs functions as a measuring cell, in some embodiments. Further embodiments provide, in a first pair of electrodes, a reference electrode exposed to a reference environment and a Nernst electrode exposed to the measured environment. A metal oxide that functions as a solid electrolyte is situated between the reference electrode and the Nernst electrode. In a second pair of electrodes, an inner pump electrode is separated from an outer pump electrode, with a metal oxide functioning as a solid electrolyte situated between the inner and outer pump electrodes. The inner pump electrode and the Nernst electrode are exposed to the environment to be measured optionally through a diffusion barrier. In operation, an external reference voltage is applied across the pump electrodes. The current needed to maintain the reference voltage across the pump electrodes provides a measure of the analyte concentration in the measured environment. For a conventional broadband lambda sensor containing such a pair of electrodes, see U.S. Pat. No. 7,083,710 B2, which is incorporated herein by reference in its entirety. Optionally, a sensor of the present invention is adapted to electrically communicate with control circuitry that smoothes operation of the sensor before the sensor has achieved standard operating conditions, such as temperature. See, for example, U.S. Pat. No. 7,177,099 B2, whiten is also incorporated herein by reference in its entirety.

Thus, certain embodiments of the present invention provide so-called narrow band sensors such as lambda sensors that fluctuate between lean and rich indications. Other embodiments provide broadband sensors such as lambda sensors that indicate the partial pressure of oxygen, and thereby the degree of leanness or richness of an air-fuel mixture.

Some embodiments provide more than two electrodes. For example, a sensor according to the present invention may contain a plurality of measuring electrodes. For another example, a sensor may comprise a plurality of reference electrodes. In another example, a sensor may comprise, or be adapted to electrically communicate with, a standard electrode or other device providing information useful to the operation of the sensor.

Additional Synthesis and Operational Techniques

Converting a metal compound, according to some embodiments of the present invention, comprises exposing the metal compound to an environment operable to convert the metal compound to a metal oxide. Environments operable to convert metal compounds to metal oxides, in some embodiments demonstrate conditions sufficient to vaporize and/or decompose the compounds and precipitate metal oxide formation. In one embodiment, an environment operable to convert metal compounds to metal oxides composes a heated environment. A metal salt of a carboxylic acid, for example, can be exposed to an environment heated to a temperature operable to evaporate the carboxylic acid and induce formation of the metal oxide. In some embodiments, the environment is heated to a temperature greater than about 200° C. In other embodiments, the environment Is heated to a temperature ranging from about 400° C. to about 650° C. In some embodiments, the environment is heated to a temperature of up to about 425° C. or up to about 450° C. In still other embodiments, the environment is heated to a temperature ranging from about 650° C. to about 800° C., or from about 800° C. to about 1000° C.

The time it takes to convert at least a portion of the at least one metal compound to at least one metal oxide depends on the conversion technique, if thermal energy is used to drive the conversion, lower temperatures generally take a longer time. In some embodiments, a metal compound composition is heated for at least 15 minutes, at least 30 minutes, at least 45 minutes, or at least one hour in other embodiments, a metal compound composition is healed for less than 15 minutes, or for more than one hour.

In some embodiments, an environment operable to convert metal compounds to metal oxides, is free or substantially free of oxygen. In other embodiments, an environment operable to convert metal compounds to metal oxides comprises oxygen.

In some embodiments, the metal compound composition is fully converted to a metal oxide composition. In some embodiments, the metal compound composition comprises a metal carboxylate, a metal alkoxide, a metal β-diketonate, or a combination thereof.

In another aspect the present invention provides methods of increasing the ionic conductivity of a solid electrolyte. A method of increasing the ionic conductivity of a solid electrolyte, in some embodiments, comprises increasing the number of grain boundaries in the solid electrolyte, wherein increasing the number of grain boundaries composes forming a plurality of nanocrystalline grains composing an electrolyte material. In some embodiments of the present invention, an electrolyte material comprises one or more metal oxides. Forming a plurality of metal oxide nanocrystalline grains comprises applying a metal compound composition to a substrate, and converting at least some of the metal compound composition to a plurality of metal oxide nanocrystalline grains.

In another aspect, the present invention provides methods of increasing the number of triple phase boundaries in a solid oxide cell comprising providing an electrolyte comprising a plurality of metal oxide nanocrystalline grains. Providing an electrolyte comprising a plurality of nanocrystalline grains, in some embodiments, comprises applying a metal compound composition to a substrate, and converting at least some of the metal compound composition to a plurality of metal oxide nanocrystalline grains. In some embodiments, the metal compound composition is fully converted into a plurality of metal oxide nanocrystalline grains. In one embodiment, the substrate comprises an electrode of a solid oxide cell.

In some embodiments of methods of the present invention, a metal compound comprises a transition metal compound. In other embodiments, a metal compound comprises a rare earth metal compound, in a further embodiment metal compound compositions comprise a plurality of metal compounds, in one embodiment, a plurality of metal compounds comprises a rare earth metal compound and a transition metal compound in still other embodiments, a metal compound comprises metal sons that are the same of different, and ligands that are the same or different in some embodiments those ligands are chosen from one or more carboxylates one or more alkoxides, one or more β-diketonates, and combinations thereof.

Moreover, in certain embodiments of the present invention, metal compound compositions can comprise liquid metal compound compositions, solid metal compound compositions, vapor metal compound compositions, or combinations thereof. In one embodiment a liquid metal carboxylate composition comprises an excess of the liquid carboxylic add used to form the metal carboxylate salt. In another embodiment, a liquid metal compound composition composes a solvent including, but not limited to, organic solvents such as benzene, toluene, xylene, chloroform, dichloromethane one or more hydrocarbons such as octane and/or other alkanes, or mixtures of any of the foregoing. The optional solvent may be any hydrocarbon and mixtures thereof. In some embodiments, the solvent can be chosen from carboxylic acids; toluene; benzene; xylene, alkanes, such as for example, propane butane, isobutene, hexane, heptane, octane, and decane; alcohols, such as methanol, ethanol, n-propanol, isopropanol, n-butanol, and isobutanol; mineral spirits; β-diketones, such as acetylacetone; ketones such as acetone, high-paraffin, aromatic hydrocarbons; and combinations of two or more of the foregoing. Some embodiments employ solvents that contain no water or water in trace amounts or greater, while other embodiments employ water as the solvent. In some embodiments, the metal compound composition further comprises at least one carboxylic acid. Some embodiments employ no solvent in the metal compound composition. Other embodiments employ no carboxylic acid in the metal compound composition. In some embodiments, solid metal compound compositions comprise metal compound powders, in a further embodiment, a vapor metal compound composition comprises a gas phase metal compound operable to condense on a substrate prior to conversion to a metal oxide. In one embodiment, a metal compound composition comprises a gel including, but not limited to a sol-gel, hydrogel, or a combination thereof.

Establishing a porosity gradient among a plurality of layers of an electrode permits the electrode to better match the porosity of the electrolyte without producing a pore structure within the electrode that is unduly restrictive to air, fuel, reactant, or product flow. Porosity can be controlled by any suitable method, such as, for example, by including particles such as nanoparticles in the compositions used to manufacture an electrode or electrolyte, pore-forming agents that release gas during manufacture, substances that can be dissolved, melted, or sublimed and thereby removed after a given layer has been manufactured, and combinations thereof.

In some embodiments, a solid oxide cell has an operating temperature less than about 1000° C. or less than about 900° C. in another embodiment a solid oxide fuel cell of the present invention has an operating temperature of less than about 800° C., less than about 700° C., less than about 600° C., or less than about 500° C. In a further embodiment a solid oxide fuel cell of the present invention has an operating temperature of less than about 300° C., less than about 200° C., or less than about 100° C.

A lower operating temperature allows non-ceramic materials such as metals and metal carbides to be used. Since these materials generally possess higher levels of mechanical or structural strength at the lower operating temperatures, they can have higher levels of porosity than either ceramics (such as the LSM that can be used for cathodes in fuel cells) or cermets (such as mixtures of nickel and zirconia that can be used for anodes in fuel cells). In other embodiments, solid oxide cells of the present invention demonstrate greater tolerance for high operating temperatures. That greater tolerance enables such cells to be constructed from less expensive materials, and may increase service lifetime. The increased tolerance for high operating temperatures stems from the greater matching of coefficients of thermal expansion available to at least some embodiments of the present invention.

In yet another aspect, the present invention provides a method of generating electric current comprising providing a solid oxide fuel cell composing an air electrode, a fuel electrode, an electrolyte interposed between the air electrode and the fuel electrode wherein fine electrolyte comprises a metal oxide and another material and has an ionic conductivity greater than the bulk ionic conductivity of the metal oxide and the other material, and optionally an electrode-electrolyte transition layer; providing a fuel to the fuel electrode; providing oxygen to the air electrode, oxidizing the fuel to generate free electrons; transporting the free electrons through an external circuit to the air electrode (cathode); and then reducing the diatomic oxygen molecules at the air electrode to oxygen anions. In some embodiments, the fuel comprises hydrogen. In other embodiments, the fuel comprises a hydrocarbon. In embodiments wherein the fuel is a hydrocarbon, methods of generating electrical current further comprise reforming the hydrocarbon fuel at the fuel electrode. Other embodiments provide cells comprising more than one cathode electrode, and/or more than one anode electrode. Still other embodiments provide a plurality of cells, wherein the cells are connected in series, in parallel, or a combination thereof.

Figure 2:
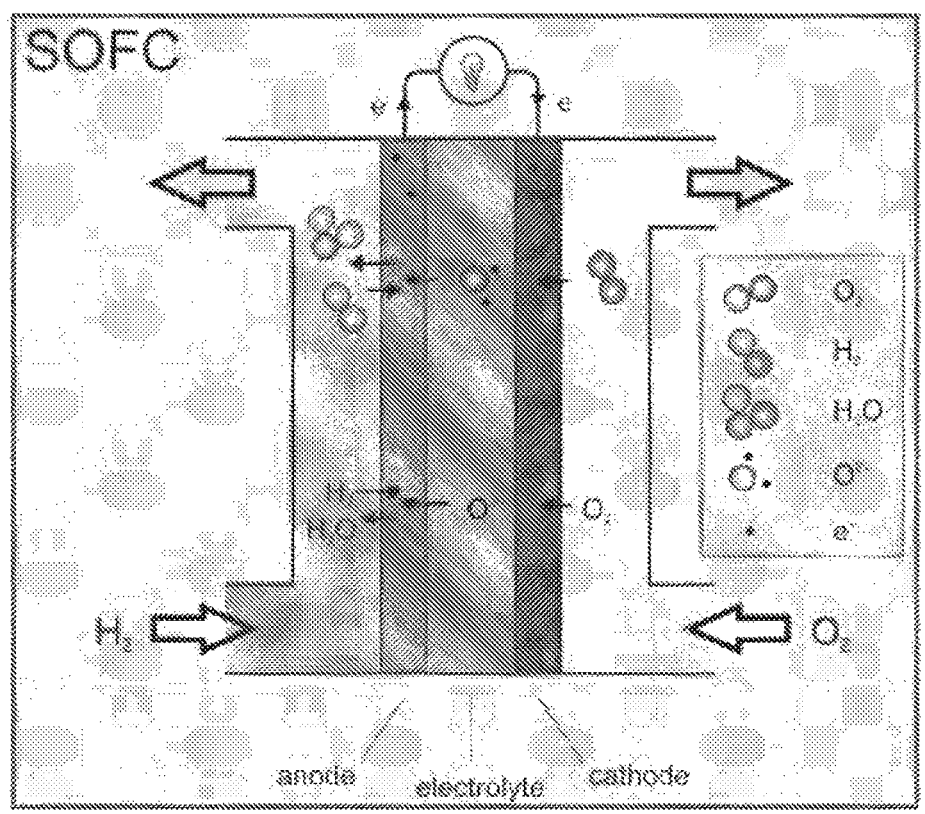
FIG. 2 illustrates a solid oxide fuel cell according to one embodiment of the present invention.

FIG. 2 illustrates a solid oxide fuel cell according to one embodiment of the present invention. As displayed in FIG. 2 the solid oxide fuel cell comprises an air electrode (cathode), a fuel electrode (anode), an electrolyte interposed between the air electrode (cathode) and the fuel electrode (anode). An electrode-electrolyte transition layer (not shown) is optionally interposed between the air electrode (cathode) and the electrolyte. The air electrode (cathode) and the fuel electrode (anode) are connected by an external circuit across which a load is applied. Oxygen ($O_2$) or a mixture of gases comprising oxygen (e.g., air) is fed to the air electrode wherein oxygen molecules are reduced to oxygen anions ($O^{2-}$). Moreover, hydrogen molecules ($H_2$) from a fuel source are oxidized at the fuel electrode. Electrons removed from hydrogen molecules at the fuel electrode travel through interconnects (not shown) to the external circuit to the air electrode (cathode) generating electric current while oxygen anions ($O^{2-}$) travel through the electrolyte to combine with hydrogen cations ($H^+$) thereby producing water ($H_2O$).

In other embodiments of the present invention, various configurations of fuel cells are contemplated. For example, more than one fuel electrode can pair with more than one air electrode. The physical configuration of the various electrodes, electrolytes, interconnects, and/or other components is not limited. In some embodiments, the configuration is optimized for size, current density, voltage, portability, fuel versatility energy conservation, specific application, aesthetics, other considerations, or combinations thereof.

EXAMPLES

Example 1

Figure 3:
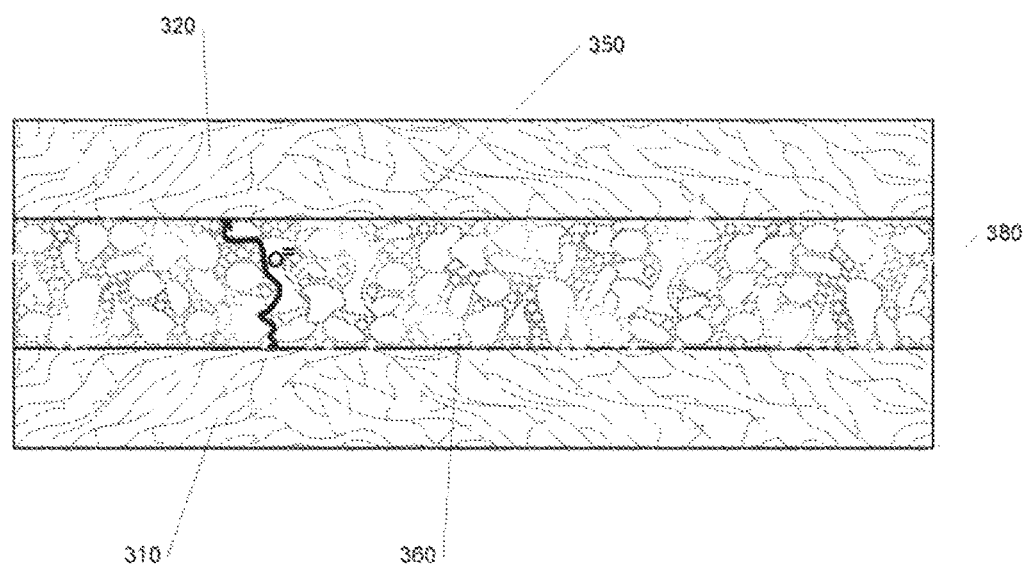
FIG. 3 partially illustrates a solid oxide cell according to one embodiment of the present invention. A first material comprising a powder 350 and a metal oxide 380 form a metal oxide electrolyte 380 between two electrodes 310, 320. When operated as a fuel cell, oxygen anions diffuse, among other places, through interfaces between the powder 350 and the metal oxide 360.

FIG. 3 depicts one embodiment of the invention in the form of a solid oxide cell having a metal oxide electrolyte 380 positioned between a first electrode 310 and a second electrode 320. The metal oxide electrolyte 380 comprises a powder 360 together with a metal oxide 360. In some cases the powder 350 can be mixed with one or more metal compounds to form a slurry that is then applied by spin coating, brushing, or other suitable method onto the first electrode 310 (or second electrode 320). Then, the metal compound is converted to form the metal oxide 360, for example, by heating the atmosphere about the metal compound, or by inductively heating the first electrode 310. Optionally, once a layer of the metal oxide electrolyte 380 has been formed, additional powder-metal compound slurry can be applied and heated to form a thicker metal oxide electrolyte 380. The cell is assembled by placing the second electrode 320 onto the metal oxide electrolyte 380, or, optionally, additional metal compound (or powder-metal compound slurry) is converted to metal oxide while contacting the metal oxide electrolyte 380 and the second electrode 320, to provide better contact between the metal oxide electrolyte 380 and the second electrode 320. In certain cases, the powder 350 is strontium titanate, and the metal oxide 380 is yttria-stabilized zirconia.

In operation, for example, air or other oxygen-containing gas is supplied to the first electrode 310, which acts as the cathode to reduce diatomic oxygen to $O^{2-}$. $O^{2-}$ (shown as $O^-$) then diffuses through the metal oxide electrolyte 380 to the second electrode 320, where the $O^{2-}$ joints $H^+$ to form water (not shown). The $H^+$ results from the oxidation of, for example, hydrogen gas at the second electrode 320, which acts as an anode. Circuitry (not shown) transmits electrons from the anode (second electrode 320) to the cathode (first electrode 310).

Example 2

Figure 4:
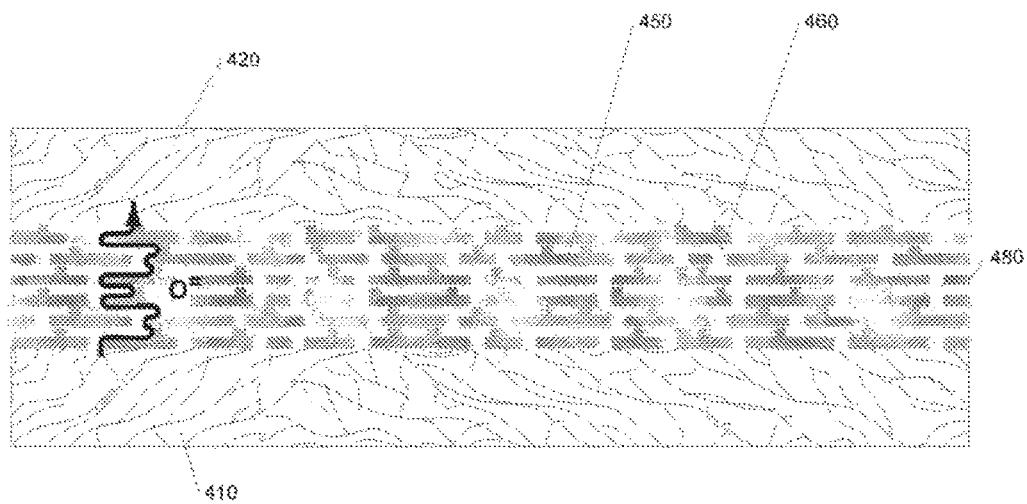
FIG. 4 partially illustrates a solid oxide cell according to one embodiment of the present invention. A first metal oxide 450 and a second metal oxide 460, disposed in interpenetrating domains of metal oxides, form a metal oxide electrolyte between two electrodes 410, 420. When operated as a fuel cell, oxygen anions diffuse, among other places, through interfaces between the first metal oxide 450 and the second metal oxide 460.

FIG. 4 depicts another embodiment of the present invention, in which a first metal oxide 450 and a second metal oxide 460, disposed in interpenetrating domains of metal oxides form a metal oxide electrolyte between two electrodes 410, 420. To form such domains, a first metal compound composition is applied to the first electrode 410 and converted to a first metal oxide 450, such as, for example, strontium titanate. Then, a second metal compound composition is applied to the first metal oxide 450 and allowed to accumulate in pores, imperfections, and defects in the first metal oxide so formed. The second metal oxide composition is converted to form a second metal oxide 460, such as, for example, yttria-stabilized zirconia. Six alternating layers of the first metal oxide 450 and the second metal oxide 460 are formed in this embodiment.

In operation, for example, air or other oxygen-containing gas is supplied to the first electrode 410, which acts as the cathode to reduce diatomic oxygen to $O^{2-}$. $O^{2-}$ (shown as $O^-$) then diffuses through the metal oxide electrolyte 480 to the second electrode 420, where the $O^{2-}$ joints $H^+$ to form water (not shown). The $H^+$ results from the oxidation of, for example, hydrogen gas at the second electrode 420, which acts as an anode. Circuitry (not shown) transmits electrons from the anode (second electrode 420) to the cathode (first electrode 410).

Example 3

Figure 5:
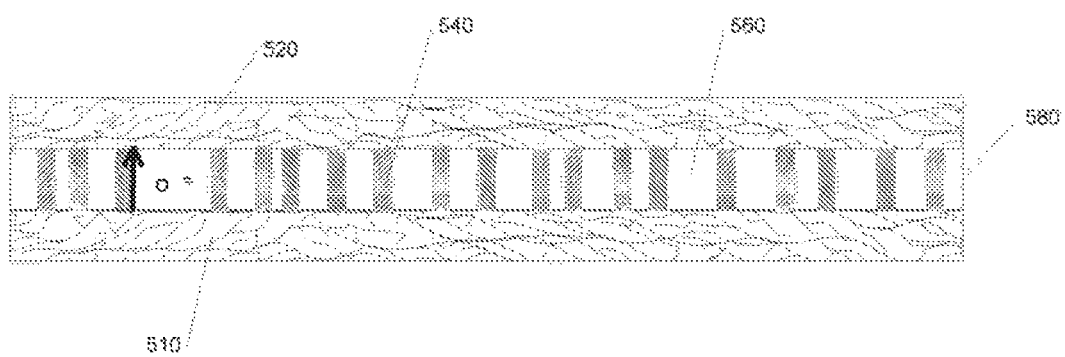
FIG. 5 partially illustrates a solid oxide cell according to one embodiment of the present invention. A nanobar 540 and a metal oxide 560, disposed so that the nanobars 540 orient substantially perpendicularly to a first planar electrode 510, form a metal oxide electrolyte between two electrodes 510, 520. When operated as a fuel cell, oxygen anions diffuse, among other places through interfaces between the nanobar 540 and the metal oxide 460.

FIG. 5 depicts a solid oxide cell according to one embodiment of the present invention. A nanobar 540 and a metal oxide 560, disposed so that the nanobars 540 orient substantially perpendicularly to a first planar electrode 510, form a metal oxide electrolyte 580 between two electrodes 510, 520. The nanobar 540 can be, for example, a multi-walled carbon nanotube of semiconductor characteristic, oriented in metal oxide 560 which can be, for example, yttria-stabilized zirconia. To make the cell of FIG. 5, chosen nanobars 540 are combined with at least one metal compound in a metal compound composition, that is then applied to the first electrode 510. An orienting force is then applied.

Optionally, the first electrode with the metal compound composition is placed in a magnetic field, at least a portion of the nanobars orient due to the magnetic field, and the metal compound composition is converted to form the metal oxide 560. Or, an electric field is applied to orient at least a portion of the nanobars 540, and the metal compound composition is converted to form the metal oxide 560. In some cases, the second electrode 520 is placed over the metal compound composition on the first electrode 510 and an electric field is established between the first electrode 510 and the second electrode 520, thereby orienting at least a portion of the nanobars 540. Then the metal compound composition is converted, such as, for example by heating, thereby forming the metal oxide 560 and the metal oxide electrolyte 580.

In operation, for example, air or other oxygen-containing gas is supplied to the first electrode 510, which acts as the cathode to reduce diatomic oxygen to $O^{2-}$. $O^{2-}$ (shown as $O^-$) then diffuses through the metal oxide electrolyte 580 to the second electrode 520, where the $O^{2-}$ joints $H^+$ to form water (not shown). The $H^+$ results from the oxidation of, for example, hydrogen gas at the second electrode 520, which acts as an anode. Circuitry (not shown) transmits from the anode (second electrode 520) to the cathode (first electrode 510).

Example 4

FIG. 6A depicts thin sheets 600 interspersed with metal oxide 660. To assemble the thin sheets 650 with metal oxide 660, a metal compound composition is applied to a first thin sheet 650, and a second thin sheet 650 is laid over the metal compound composition. Then, the metal compound composition is converted to a metal oxide. Additional metal compound composition (which in other embodiments may be different from the metal compound composition applied to the first thin sheet 650) is applied to the exposed surface of the second thin sheet 650, and a third thin sheet 650 is laid over the metal compound composition. That metal compound composition is then converted to form the metal oxide 660. Accordingly, additional thin sheets 650 and additional metal oxide 660 are assembled, in this embodiment. Alternatively, multiple thin sheets 650 can be coated with metal compound composition held together under a mild compressive force, and heated to convert the metal compound into metal oxide 660. In still another variant, each thin sheet 650 can have metal compound applied on both sides, and the metal compound is then converted into metal oxide 660. Thin sheets 650 thus coated on both sides with metal oxide 660 can then be assembled together. Optionally, one or more epoxies (not shown) can assist to hold the thin sheets 650 and metal oxide 660 together.

The thin sheets 650 and metal oxide 660 of FIG. 6A can be sliced along plane "A" and assembled into cells of the present invention. FIG. 6B shows the assembly of thin sheets 650 and metal oxide 660 depicted in FIG. 6A as if cut along "A". Two planar electrodes sandwiching the assembly of FIG. 6B form a cell in one embodiment of the present invention. In operation, ions would diffuse substantially parallel to the thin sheets 650. In some embodiments, the thin sheets 650 are mica, and the metal oxide 660 is yttria-stabilized zirconia.

Example 5

FIG. 7A depicts thin sheets 750 such as mica formed into flat annular discs, such as by cutting and pressing hot mica, and arranged in space so the discs are substantially parallel. As in Example 4, the thin sheets 750 can be coated with metal oxide (not shown) in any suitable manner and sequence.

The thin sheets 750 of FIG. 7A (together with metal oxide, not shown) can be assembled between an outer tubular electrode 710 and an inner tubular electrode 720 to form a metal oxide electrolyte 780 shown in FIG. 7B. The outer tubular electrode 710 and inner tubular electrode 720 shown are circular in cross-section, in other embodiments, tubes having any suitable cross-section may be used in operation, for example, as a solid oxide fuel cell, fuel such as hydrogen-containing gas is introduced in cavity 790 where if is oxidized at inner tubular electrode 720, which acts as an anode. Oxygen-containing gas such as air contacts the outer tubular electrode 710, which acts as a cathode reducing oxygen to $O^{2-}$. The oxygen anions migrate from the outer tubular electrode 710 through the metal oxide electrolyte 780 to the inner tubular electrode 720, where the oxygen anions combine with protons to form water, which flows out of the call through cavity 790. External circuitry (not shown) completes the circuit between the outer tubular electrode 710 and the inner tubular electrode 720. Optionally, outer tubular electrode 710 and/or inner tubular electrode 720 are porous. In another example, one or more epoxies (not shown) can help seal and/or hold together the metal oxide electrolyte 780.

Example 6

Figure 8:
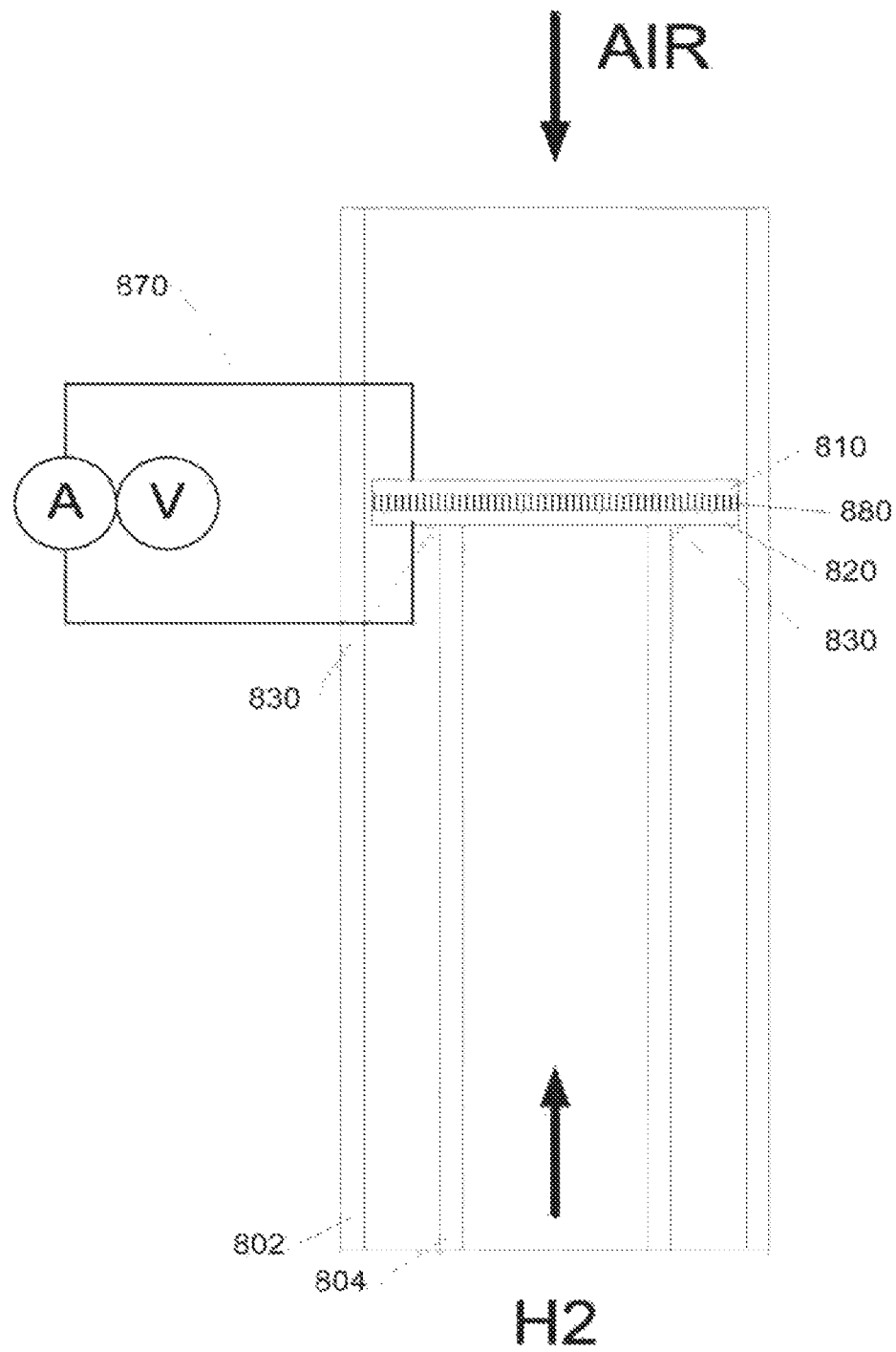
FIG. 8 partially depicts a solid oxide cell according to a further embodiment of the present invention, optionally operable to test a metal oxide electrolyte 880 for enhanced some conductivity. A cathode 810 and an anode 820 sandwich a metal oxide electrolyte to test performance with external circuitry 870.

FIG. 8 depicts a side cut-away view of a solid oxide cell according to an embodiment of the present invention, optionally operable to test a metal oxide electrolyte 880 for enhanced ionic conductivity. A cathode 810 and an anode 820 sandwich a metal oxide electrolyte 880 to test performance with external circuitry 870. An inner tube 804, for example glass, supports the cell by way of an annular seal 830, which comprises one or more epoxies. The inner tube 804 supplies a hydrogen-containing gas (H2) to the second electrode 820, which acts as an anode. First electrode 810 acts as a cathode, reducing oxygen in an oxygen-containing gas (AIR) to $O^{2-}$, which then migrates through metal oxide electrolyte 880 to the second electrode 820. Outer tube 802 contains the cell and optionally allows control over the oxygen content and the temperature of the cell. External circuitry 870 creates a circuit from first electrode 810 to second electrode 820, and allows determination of oxygen anion conductivity of metal oxide electrolyte 880 using an ampmeter (A) and a voltimeter (V).

EMBODIMENTS

Embodiment 1

A method of enhancing some conductivity in a metal oxide electrolyte comprising a first material and a metal oxide comprising:
applying a metal compound to the first material; and
converting at least some of the metal compound to form the metal oxide;
wherein the first material and the metal oxide have an ionic conductivity greater than the hulk ion in conductivity of the first material and of the metal oxide.

Embodiment 2

The method of embodiment 1, wherein the first material comprises crystalline material.

Embodiment 3

The method of embodiment 2, wherein the crystalline material composes nanocrystalline material.

Embodiment 4

The method of embodiment 1, wherein the first material comprises a metal oxide.

Embodiment 5

The method of embodiment 1, wherein the first material is chosen from strontium titanate, titania, alumina, zirconia, yttria-stabilized zirconia, alumina-doped yttria-stabilized zirconia, iron-doped zirconia, magnesia, ceria, samarium-doped ceria, gadolinium-doped ceria, and combinations thereof.

Embodiment 6

The method of embodiment 5, wherein the first material is chosen from alumina, titania, zirconia, yttria-stabilized zirconia, alumina-doped yttria-stabilized zirconia, iron-doped zirconia, magnesia, ceria, samarium-doped ceria, gadolinium-doped ceria, and combinations thereof.

Embodiment 7

The method of embodiment 1, wherein the first material composes mica.

Embodiment 8

The method of embodiment 1, wherein the metal oxide is chosen from strontium titanate, titania, alumina, zirconia, yttria-stabilized zirconia, alumina-doped yttria-stabilized zirconia, iron-doped zirconia, magnesia, ceria, samarium-doped ceria, gadolinium-doped ceria, and combinations thereof.

Embodiment 9

The method of embodiment 8, wherein the metal oxide is chosen from alumina, titania, zirconia, yttria-stabilized zirconia, alumina-doped yttria-stabilized zirconia, iron-doped zirconia, magnesia, ceria, samarium-doped ceria, gadolinium-doped ceria, and combinations thereof.

Embodiment 10

The method of embodiment 1, wherein the first material comprises strontium titanate, and the metal oxide comprises yttria-stabilized zirconia.

Embodiment 11

The method of embodiment 10, wherein the yttria-stabilized zirconia composes from about 10 mol % to about 20 mol % yttria.

Embodiment 12

The method of embodiment 10, wherein the yttria-stabilized zirconia comprises from about 12 mol % to about 18 mol % yttria.

Embodiment 13

The method of embodiment 10, wherein the yttria-stabilized zirconia comprises from about 14 mol % to about 16 mol % yttria.

Embodiment 14

The method of embodiment 1, wherein the first material comprises magnesia, and the metal oxide comprises yttria-stabilized zirconia.

Embodiment 15

The method of embodiment 1, wherein the first material comprises titania, and the metal oxide comprises yttria-stabilized zirconia.

Embodiment 16

The method of embodiment 1, wherein the first material comprises strontium titanate, and the metal oxide comprises iron-doped zirconia.

Embodiment 17

The method of embodiment 1, wherein the first material comprises samarium-doped ceria, and the metal oxide comprises ceria.

Embodiment 18

The method of embodiment 1, further comprising applying an epoxy to the metal oxide.

Embodiment 19

A metal oxide electrolyte comprising:
a first material and a metal oxide, wherein the metal oxide is formed by applying a metal compound to the first material; and
converting at least some of the metal compound to form the metal oxide,
wherein the first material and the metal oxide have an ionic conductivity greater than the bulk ionic conductivity of the first material and of the metal oxide.

Embodiment 20

A method for forming a metal oxide electrolyte, comprising:
applying a metal compound to a first material in powder form; and
converting at least some of the metal compound to form a metal oxide, thereby forming the metal oxide electrolyte;
wherein the metal oxide electrolyte has an ionic conductivity greater than the bulk ionic conductivity of the first material and of the metal oxide.

Embodiment 21

The method of embodiment 20, wherein the first material in powder form comprises strontium titanate, and the metal oxide comprises yttria-stabilized zirconia.

Embodiment 22

The method of embodiment 20, wherein the first material in powder form comprises mica, and the metal oxide comprises yttria-stabilized zirconia, gadolinium-doped ceria, alumina, or a combination thereof.

Embodiment 23

The method of embodiment 20, further comprising applying an orienting force before, during, or before and during the converting.

Embodiment 24

The method of embodiment 23, wherein the orienting force is chosen from magnetic fields, electric fields, and combinations thereof.

Embodiment 25

A method for forming a metal oxide electrolyte comprising:
applying a first metal compound to a substrate;
converting at least some of the first metal compound to form a first metal oxide on the substrate;
applying a second metal compound to the substrate composing the first metal oxide; and
converting at least some of the second metal compound to form a second metal oxide on the substrate comprising the first metal oxide,
thereby forming the metal oxide electrolyte;
wherein the metal oxide electrolyte has an ionic conductivity greater than the bulk ionic conductivity of the first metal oxide and of the second metal oxide.

Embodiment 25

The method of embodiment 25, further comprising
applying additional first metal compound to the substrate composing the first metal oxide and the second metal oxide; and
converting at least some of the additional first metal compound to form additional first metal oxide.

Embodiment 27

The method of embodiment 26, further comprising
applying additional second metal compound to the additional first metal oxide; and
converting at least, some of the additional second metal compound to form additional second metal oxide.

Embodiment 28

A method for forming a metal oxide electrolyte, comprising:
applying a metal compound to a first material in nanobar form; and
converting at least some of the metal compound to form a metal oxide, thereby forming the metal oxide electrolyte;
wherein the metal oxide electrolyte has an ionic conductivity greater than the bulk ionic conductivity of the first material and of the metal oxide.

Embodiment 29

The method of embodiment 28, wherein the nanobar form is chosen from nanorods, single-walled nanotubes, multi-walled nanotubes, and combinations thereof.

Embodiment 30

The method of embodiment 28, wherein the first material in nanobar form is present in the metal oxide electrolyte conforming to an orientation.

Embodiment 31

The method of embodiment 30, wherein the orientation is caused by a magnetic field applied before, during, or before and during the converting.

Embodiment 32

The method of embodiment 31, wherein the magnetic field is chosen from static magnetic fields, variable magnetic fields, uniform magnetic fields, non-uniform magnetic fields, and combinations thereof.

Embodiment 33

The method of embodiment 30, wherein the orientation is caused by an electric field applied before, during, or before and during the converting.

Embodiment 34

The method of embodiment 28, wherein the first material in nanobar form comprises strontium titanate, and the metal oxide comprises yttria-stabilized zirconia.

Embodiment 35

A method for forming a metal oxide electrolyte comprising:
applying a metal compound to a thin sheet; and
converting as least some of the metal compound to form a metal oxide on the thin sheet, thereby forming the metal oxide electrolyte;
wherein the metal oxide electrolyte has an ionic conductivity greater than the bulk ionic conductivity of the thin sheet and of the metal oxide.

Embodiment 36

The method of embodiment 35, further comprising applying an epoxy to the metal oxide electrolyte.

Embodiment 37

The method of embodiment 35, further comprising applying an epoxy to the metal oxide.

Embodiment 38

A method for making a metal oxide electrolyte, comprising:
applying a nanobar functionalized with a metal compound to a substrate; and
converting the metal compound to a metal oxide thereby forming the metal oxide electrolyte;
wherein the metal oxide electrolyte has an ionic conductivity greater than the bulk some conductivity of the metal oxide.

Embodiment 39

The method of embodiment 38, wherein the nanobar functionalized with a metal compound is oriented before the converting.

Embodiment 40

The method of embodiment 39, wherein the nanobar functionalized with a metal compound is oriented by the applying.

Embodiment 41

The method of embodiment 39, wherein the nanobar functionalized with a metal compound is oriented by brushing, spin coating, a magnetic field, an electric field or a combination thereof.

Embodiment 42

A solid oxide cell comprising:
an inner tubular electrode having an outer surface;
an outer electrode; and
a metal oxide electrolyte adapted to provide ionic conductivity between the inner tubular electrode and the outer electrode;
wherein the metal oxide electrolyte comprises a plurality of thin sheets oriented substantially perpendicular to the outer surface of the inner tubular electrode, and a metal oxide contacting the thin sheets.

Various embodiments of the invent-on have been described in fulfillment of the various objects of the invention, it should be recognized that these embodiments are merely illustrative of the principles of the present invention. Furthermore, the foregoing description of various embodiments does not necessarily imply exclusion. For example, "some" embodiments may include all or part of "other" and "further" embodiments. Numerous modifications and adaptations thereof will be readily apparent to those skilled in the art without departing from the spirit and scope of the invention. As used throughout this document and the claims, "a" does not necessarily mean "one and only one." Unless otherwise indicated "a" can mean "at least one" For example, "a metal oxide electrolyte comprising a first material and a metal oxide" indicates a metal oxide electrolyte that comprises one or more materials (which may include a metal oxide), and one or more metal oxides.

We claim:

1. A solid oxide cell, comprising:
an inner tubular electrode having an outer surface;
an outer electrode; and
a metal oxide electrolyte adapted to provide ionic conductivity between the inner tubular electrode and the outer electrode;
wherein the metal oxide electrolyte comprises a plurality of thin sheets oriented substantially perpendicular to the outer surface of the inner tubular electrode, and a metal oxide contacting the thin sheets;
wherein the thin sheets are mica.

2. The solid oxide cell of claim 1, wherein the solid oxide cell is a solid oxide fuel cell.

3. The solid oxide cell of claim 2,
wherein the inner tubular electrode is adapted to contact a hydrogen-containing gas and act as an anode; and
wherein the outer electrode is adapted to contact an oxygen-containing gas and act as a cathode.

4. The solid oxide cell of claim 1, wherein the metal oxide comprises yttria-stabilized zirconia.

5. The solid oxide cell of claim 4, wherein the yttria-stabilized zirconia comprises from about 10 mol % to about 20 mol % yttria.

6. The solid oxide cell of claim 4, wherein the yttria-stabilized zirconia comprises from about 12 mol % to about 18 mol % yttria.

7. The solid oxide cell of claim 4, wherein the yttria-stabilized zirconia comprises from about 14 mol % to about 16 mol % yttria.

8. The solid oxide cell of claim 1, wherein the metal oxide electrolyte comprises at least one catalytic material chosen from platinum, palladium, rhodium, nickel, cerium, gold, silver, zinc, lead, ruthenium, rhenium, or a mixture thereof.

9. The solid oxide cell of claim 1, wherein the outer electrode is an outer tubular electrode.

\* \* \* \* \*